(12) United States Patent
Yu et al.

(10) Patent No.: US 8,703,425 B2
(45) Date of Patent: Apr. 22, 2014

(54) BIOMARKER FOR GASTRIC CANCER

(75) Inventors: Jun Yu, Ma On Shan (HK); Joseph Jao Yiu Sung, Shatin (HK); Xiaoxing Li, Shatin (HK); Lixia Xu, Shatin (HK)

(73) Assignee: The Chinese University of Hong Kong, Shatin, N.T., Hong Kong (CN)

( * ) Notice: Subject to any disclaimer, the term of this patent is extended or adjusted under 35 U.S.C. 154(b) by 233 days.

(21) Appl. No.: 13/230,670

(22) Filed: Sep. 12, 2011

(65) Prior Publication Data

US 2013/0065836 A1    Mar. 14, 2013

(51) Int. Cl.
*C12Q 1/68* (2006.01)

(52) U.S. Cl.
USPC .......................................... 435/6.14; 435/6.1

(58) Field of Classification Search
None
See application file for complete search history.

(56) References Cited

U.S. PATENT DOCUMENTS

| | | | |
|---|---|---|---|
| 7,306,913 B2 * | 12/2007 | Devlin et al. | 435/6.11 |
| 2007/0161031 A1 * | 7/2007 | Trinklein et al. | 435/6 |

FOREIGN PATENT DOCUMENTS

| | | | | |
|---|---|---|---|---|
| WO | WO2004166519 | * | 7/2004 | C07H 21/84 |
| WO | WO2010006215 | * | 1/2010 | C12Q 1/68 |

OTHER PUBLICATIONS

Tao, Qian, et al., "Defective de novo methylation of viral and cellular DNA Sequences in ICF Syndrome Cells," Human Molecular Genetics, 2002, vol. 11, No. 18, 2091-2102.

Sakashita, Chizuko, et al., "Cloning and Characterization of the Human BAZF Gene, a Homologue of the BCL6 Oncogene," Biochemical and Biophysical Research Communications, 291, 2002, 567-573.

Takai, Daiya, et al. "The CpG Island Searcher: a New WWW Resource," In Silico Biology, 3, 2003, 235-240.

* cited by examiner

*Primary Examiner* — Maury Audet
(74) *Attorney, Agent, or Firm* — Kilpatrick Townsend & Stockton LLP

(57) ABSTRACT

The present invention provides a method for diagnosing and determining prognosis of gastric cancer in a subject by detecting suppressed expression of the BCL6B gene, which in some cases is due to elevated methylation level in the genomic sequence of this gene. A kit and device useful for such a method are also provided. In addition, the present invention provides a method for treating gastric cancer by increasing BCL6B gene expression or activity.

4 Claims, 10 Drawing Sheets

Adjacent normal, upper 200x, lower 400x.    Gastric cancer, upper 200x, lower 400x.

ID NO:9, 18, 19, or 20, or even the full length of SEQ ID
BIOMARKER FOR GASTRIC CANCER

REFERENCE TO A "SEQUENCE LISTING," A TABLE, OR A COMPUTER PROGRAM LISTING APPENDIX SUBMITTED AS AN ASCII TEXT FILE

The Sequence Listing written in file 16285-95.TXT, created on Nov. 7, 2011, 20,480 bytes, machine format IBM-PC, MS-Windows operating system, is hereby incorporated by reference in its entirety for all purposes.

BACKGROUND OF THE INVENTION

Gastric cancer, also known as stomach cancer, is the fourth most common cancer worldwide with approximately 1,000,000 cases diagnosed annually. It is a disease with a high mortality rate (about 800,000 deaths per year), making it the second most common cause of cancer death worldwide after lung cancer. The incidence of gastric cancer is significantly higher among men and in developing nations, including many Asian countries.

Gastric cancer often remains asymptomatic or exhibits only nonspecific symptoms in its early stages, diagnosis in many cases is therefore not made until the disease has reached an advanced stage. This leads to a generally poor prognosis: metastasis occurs in 80-90% of individuals diagnosed with gastric cancer, with a six-month survival rate of 65% in those diagnosed in early stages and less than 15% of those diagnosed in late stages.

Because of the prevalence of gastric cancer and its grave implications on patients' life expectancy, there exists a need for new methods to diagnose, monitor, and treat gastric cancer. This invention fulfills this and other related needs.

BRIEF SUMMARY OF THE INVENTION

In a first aspect, the present invention provides a method for detecting gastric cancer in a subject. The method includes the steps of: (a) measuring expression level of BCL6B in a sample taken from the subject, and (b) comparing the expression level obtained in step (a) with a standard control. When a decrease in the expression level of BCL6B is detected as compared with the standard control, it indicates that the subject may have gastric cancer. Typically, the sample used in the method is a stomach mucosa sample, e.g., one that includes stomach epithelial cells.

In some embodiments, the expression level of BCL6B is BCL6B protein level. In other embodiments, the expression level of BCL6B mRNA level. When the BCL6B protein level is measured, step (a) may include an immunoassay using an antibody that specifically binds the BCL6B protein. For example, a Western Blot analysis may be used. In other cases, step (a) may involve mass spectrometry, or a hybridization-based assay such as hybridization to a microarray, fluorescence probe, or molecular beacon.

In some embodiments, step (a) may involve an amplification reaction, such as a polymerase chain reaction (PCR), especially a reverse transcriptase-PCR(RT-PCR). In some cases, the detecting step involves a polynucleotide hybridization assay, for example, a Southern Blot analysis, Northern Blot analysis, or in situ hybridization assay. In some cases, a polynucleotide probe is used in the polynucleotide hybridization assay to hybridize with SEQ ID NO:9, 10, 11, 12, 18, 19, or 20 or a complement thereof. Optionally, the polynucleotide probe includes or has a detectable moiety attached to it.

In certain embodiments, when a subject being tested for gastric cancer is first indicated as having gastric cancer, the method may further include a repeated step (a) at a later time using the sample type of sample from the subject (i.e., collected from the general tissue type or anatomic location of the stomach by the same or similar manner). When an increase is observed in the expression level of BCL6B (either protein or mRNA) at the later time as compared to the amount from the original step (a), it indicates an improvement of gastric cancer, whereas a decrease indicates a worsening of gastric cancer.

In a second aspect, the present invention provides a method for detecting gastric cancer in a subject. The method includes these steps: (a) treating a sample taken from the subject with an agent that differentially modifies methylated and unmethylated DNA; and (b) after treatment of step (a), analyzing (such as sequencing) a CpG-containing genomic sequence, which is at least a segment of SEQ ID NO:9, 18, 19, or 20 (up to and including the full length of SEQ ID NO:9, 18, 19, or 20) and contains at least one CpG dinucleotide pair, to determine whether each CpG in is methylated or unmethylated. The presence of one methylated CpG in the CpG-containing genomic sequence indicates that the subject may have gastric cancer.

In some embodiments, the CpG-containing genomic sequence contains two or more CpG, for example, at least 2, 3, 4, 5, 6, 7, 8, 9, 10, or more CpG pairs, and when at least 50% of all CpG being methylated indicates that the subject may have gastric cancer. The length of the CpG-containing genomic sequence may vary but is long enough to include at least one CpG. Typically, the CpG-containing genomic sequence is a segment of at least 15 contiguous nucleotides of SEQ ID NO:9, 18, 19, or 20, and can be a segment of at least 20, 30, 50, 100, 200, or more contiguous nucleotides of SEQ ID NO:9, 18, 19, or 20, or even the full length of SEQ ID NO:9, 18, 19, or 20. In one example, the CpG-containing genomic sequence is a segment of the BCL6B promoter sequence −95 to +95 bp (SEQ ID NO:18) relative to the transcription start site. In another example, the CpG-containing genomic sequence is SEQ ID NO:19, which contains 9 CpG sites. At least 5 of all CpG being methylated indicates the subject having gastric cancer.

Typically, the sample is a stomach mucosa sample, or a stomach tissue sample comprising epithelial cells. The claimed method may further include some repeat steps. For example, when the subject being examined is indicated as having gastric cancer, steps (a) and (b) may be repeated at a later time using the sample type of sample from the subject (i.e., collected from the general tissue type or anatomic location of the stomach by the same or similar manner). An increase in the number of methylated CpG at the later time as compared to the number of methylated CpG determined from the original step (b) indicates a worsening of gastric cancer, whereas a decrease indicates an improvement of gastric cancer.

In some embodiments, the agent that differentially modifies methylated DNA and unmethylated DNA is an enzyme that preferentially cleaves methylated DNA, an enzyme that preferentially cleaves unmethylated DNA, or a bisulfite. In other embodiments, step (b) includes an amplification reaction and/or a process of sequencing of a DNA molecule.

In a third aspect, the present invention provides a kit for detecting gastric cancer in a subject. The kit contains (1) a standard control that provides an average amount of BCL6B protein or BCL6B mRNA; and (2) an agent that specifically and quantitatively identifies BCL6B protein or BCL6B mRNA. In some cases, the agent may be an antibody that specifically binds the BCL6B protein, or the agent may be a polynucleotide probe that hybridizes with the BCL6B mRNA. For example, the polynucleotide probe has the nucleotide sequence set forth in SEQ ID NO:12. Typically, the agent includes a detectable moiety. In some cases, the kit may include some additional components, such as two oligonucleotide primers for specifically amplifying at least a segment of SEQ ID NO:10 or 11 or the complement of such sequence in an amplification reaction. In some cases, the kit will further include an instruction manual.

In a fourth aspect, the present invention provides a method for inhibiting gastric cancer cell growth. The method comprising the step of contacting the gastric cancer cell with an effective amount of (1) a polypeptide comprising the amino acid sequence set forth in SEQ ID NO:17; (2) a nucleic acid comprising a polynucleotide sequence encoding SEQ ID NO:17; or (3) a demethylating agent (such as 5-aza-2'-deoxycytidine, or 5-Aza). In some cases, the nucleic acid is an expression cassette comprising a promoter operably linked to the polynucleotide sequence encoding SEQ ID NO:17, such as a nucleic acid that comprises the nucleotide sequence set forth in SEQ ID NO:10 or 11. Optionally, the promoter is an epithelium-specific promoter. The method of suppressing gastric cancer cell growth may be practiced in vitro (e.g., when gastric cancer cells are in a cell culture), ex vivo (e.g., when gastric cancer cells taken from a patient and then maintained in a cell culture), or in vivo (e.g., when the gastric cancer cell is within a patient's body).

In a fifth aspect, the present invention provides an isolated nucleic acid derived from the cDNA or genomic sequence of the BCL6B gene, which may be useful as a probe or primer for the detection or amplification of BCL6B sequences. The nucleic acid may have the nucleotide sequence at least 95% identical, optionally 100% identical, to a segment of about 20-100 contiguous nucleotides of SEQ ID NO:9, 10, 11, 12, 18, 19, or 20, or it may have the nucleotide sequence that is the complement of such a segment. In some embodiments, the nucleic acid is conjugated to a detectable moiety.

In addition, the present invention provides a kit for detecting gastric cancer. The kit comprises: (1) an agent that differentially modifies methylated and unmethylated DNA, and (2) an indicator that, after the agent has been used to treat a sample from a subject who is being tested for gastric cancer, determines whether each CpG in a CpG-containing genomic sequence is methylated or unmethylated. The CpG-containing genomic sequence is at least a segment of SEQ ID NO:9, 18, 19, or 20 and comprises at least one CpG. The present invention also provides a composition for inhibiting growth of a gastric cancer cell. The composition contains an effective amount of (1) a polypeptide comprising the amino acid sequence set forth in SEQ ID NO:17 (e.g., a polypeptide consisting of the amino acid sequence of SEQ ID NO:17) or (2) a nucleic acid comprising a polynucleotide sequence encoding SEQ ID NO:17 (e.g., a nucleic acid sequence comprising the polynucleotide sequence of SEQ ID NO:10 or 11), and a pharmaceutically acceptable carrier. In this regard, this invention provides the use of a polypeptide comprising the amino acid sequence set forth in SEQ ID NO:17 (e.g., a polypeptide consisting of the amino acid sequence of SEQ ID NO:17) or a nucleic acid comprising a polynucleotide sequence encoding SEQ ID NO:17 (e.g., a nucleic acid sequence comprising the polynucleotide sequence of SEQ ID NO:10 or 11) in preparing a medicament for inhibiting growth of a gastric cancer cell. Furthermore, the present invention provides a use of a polynucleotide sequence that comprises or consists of a segment of SEQ ID NO:9, 10, 11, 12, 18, 19, or 20 or complement thereof in preparing a kit for detecting gastric cancer. The segment is typically about 20-100 contiguous nucleotides of SEQ ID NO:9, 10, 11, 12, 18, 19, or 20.

DEFINITIONS

Figure 1:
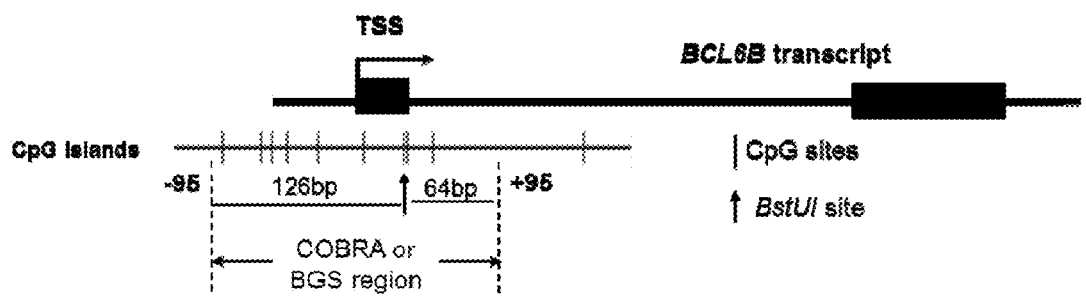
FIG. 1 shows BCL6B CpG islands in an embodiment.

The term "BCL6B gene" or "BCL6B protein," as used herein, refers to any naturally occurring variants or mutants, interspecies homologs or orthologs, or man-made variants of human BCL6B gene or BCL6B protein. The human BCL6B gene is located on chromosome 17p13.1 (Sakashita et al., *Biochem Biophys Res Commun*, 291, 567-573, 2002). The cDNA sequence of a human wild-type BCL6B gene is set forth in GenBank Accession No. NM_181844.3 (provided herein as SEQ ID NO:11), encoding a 480-amino acid BCL6B protein (provided herein as SEQ ID NO:17), a transcription repressor. A BCL6B protein within the meaning of this application typically has at least 80%, or 90%, or 95% or higher sequence identity to the human wild-type BCL6B protein.

In this disclosure the terms "gastric cancer" and "stomach cancer" have the same meaning and refer to a cancer of the stomach or of stomach cells. Such cancers may be adenocarcinomas that occur in the lining of the stomach (mucosa or stomach epithelium) and may be in pylorus, body, or cardial (lower, body and upper) parts of the stomach. A "gastric cancer cell" is a stomach epithelial cell possessing characteristics of gastric cancer and encompasses a precancerous cell, which is in the early stages of conversion to a cancer cell or which is predisposed for conversion to a cancer cell. Such cells may exhibit one or more phenotypic traits characteristic of the cancerous cells.

In this disclosure the term "or" is generally employed in its sense including "and/or" unless the content clearly dictates otherwise.

As used herein, the term "gene expression" is used to refer to the transcription of a DNA to form an RNA molecule encoding a particular protein (e.g., human BCL6B protein) or the translation of a protein encoded by a polynucleotide sequence. In other words, both mRNA level and protein level encoded by a gene of interest (e.g., human BCL6B gene) are encompassed by the term "gene expression level" in this disclosure.

In this disclosure the term "biological sample" or "sample" includes sections of tissues such as biopsy and autopsy samples, and frozen sections taken for histologic purposes, or processed forms of any of such samples. Biological samples include blood and blood fractions or products (e.g., serum, plasma, platelets, red blood cells, and the like), sputum or saliva, lymph and tongue tissue, cultured cells, e.g., primary cultures, explants, and transformed cells, stool, urine, stomach biopsy tissue etc. A biological sample is typically obtained from a eukaryotic organism, which may be a mammal, may be a primate and may be a human subject.

In this disclosure the term "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (e.g., tongue, colon, prostate, kidney, bladder, lymph node, liver, bone marrow, blood cell, stomach tissue, etc.) among other factors. Representative biopsy techniques include, but are not limited to, excisional biopsy, incisional biopsy, needle biopsy, surgical biopsy, and bone marrow biopsy and may comprise colonoscopy. A wide range of biopsy techniques are well known to those skilled in the art who will choose between them and implement them with minimal experimentation.

In this disclosure the term "isolated" nucleic acid molecule means a nucleic acid molecule that is separated from other nucleic acid molecules that are usually associated with the isolated nucleic acid molecule. Thus, an "isolated" nucleic acid molecule includes, without limitation, a nucleic acid molecule that is free of nucleotide sequences that naturally flank one or both ends of the nucleic acid in the genome of the organism from which the isolated nucleic acid is derived (e.g., a cDNA or genomic DNA fragment produced by PCR or restriction endonuclease digestion). Such an isolated nucleic acid molecule is generally introduced into a vector (e.g., a cloning vector or an expression vector) for convenience of manipulation or to generate a fusion nucleic acid molecule. In addition, an isolated nucleic acid molecule can include an engineered nucleic acid molecule such as a recombinant or a synthetic nucleic acid molecule. A nucleic acid molecule existing among hundreds to millions of other nucleic acid molecules within, for example, a nucleic acid library (e.g., a cDNA or genomic library) or a gel (e.g., agarose, or polyacrylamine) containing restriction-digested genomic DNA, is not an "isolated" nucleic acid.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain; it includes regions preceding and following the coding region (leader and trailer) involved in the transcription/translation of the gene product and the regulation of the transcription/translation, as well as intervening sequences (introns) between individual coding segments (exons).

In this application, the terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "amino acid" refers to refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. For the purposes of this application, amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. For the purposes of this application, amino acid mimetics refers to chemical compounds that have a structure that is different from the general chemical structure of an amino acid, but that functions in a manner similar to a naturally occurring amino acid.

Amino acids may include those having non-naturally occurring D-chirality, as disclosed in WO01/12654, which may improve the stability (e.g., half life), bioavailability, and other characteristics of a polypeptide comprising one or more of such D-amino acids. In some cases, one or more, and potentially all of the amino acids of a therapeutic polypeptide have D-chirality.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

As used in herein, the terms "identical" or percent "identity," in the context of describing two or more polynucleotide or amino acid sequences, refer to two or more sequences or subsequences that are the same or have a specified percentage of amino acid residues or nucleotides that are the same (for example, a variant BCL6B protein used in the method of this invention (e.g., for treating gastric cancer) has at least 80% sequence identity, preferably 85%, 90%, 91%, 92%, 93, 94%, 95%, 96%, 97%, 98%, 99%, or 100% identity, to a reference sequence, e.g., a wild-type human BCL6B protein), when compared and aligned for maximum correspondence over a comparison window, or designated region as measured using one of the following sequence comparison algorithms or by manual alignment and visual inspection. Such sequences are then said to be "substantially identical." With regard to polynucleotide sequences, this definition also refers to the complement of a test sequence. Preferably, the identity exists over a region that is at least about 50 amino acids or nucleotides in length, or more preferably over a region that is 75-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

Examples of algorithms that are suitable for determining percent sequence identity and sequence similarity are the BLAST and BLAST 2.0 algorithms, which are described in Altschul et al., (1990) *J. Mol. Biol.* 215: 403-410 and Altschul et al. (1977) *Nucleic Acids Res.* 25: 3389-3402, respectively. Software for performing BLAST analyses is publicly available at the National Center for Biotechnology Information website, ncbi.nlm.nih.gov. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff and Henikoff, *Proc. Natl. Acad. Sci. USA* 89:10915 (1989)).

The BLAST algorithm also performs a statistical analysis of the similarity between two sequences (see, e.g., Karlin and Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

In this disclosure the terms "stringent hybridization conditions" and "high stringency" refer to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993) and will be readily understood by those skilled in the art. Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous references, e.g., Current Protocols in Molecular Biology, ed. Ausubel, et al.

An "expression cassette" is a nucleic acid construct, generated recombinantly or synthetically, with a series of specified nucleic acid elements that permit transcription of a particular polynucleotide sequence in a host cell. An expression cassette may be part of a plasmid, viral genome, or nucleic acid fragment. Typically, an expression cassette includes a polynucleotide to be transcribed, operably linked to a promoter. "Operably linked" in this context means two or more genetic elements, such as a polynucleotide coding sequence and a promoter, placed in relative positions that permit the proper biological functioning of the elements, such as the promoter directing transcription of the coding sequence. Other elements that may be present in an expression cassette include those that enhance transcription (e.g., enhancers) and terminate transcription (e.g., terminators), as well as those that confer certain binding affinity or antigenicity to the recombinant protein produced from the expression cassette.

The term "bisulfite" as used herein encompasses all types of bisulfites, such as sodium bisulfite, that are capable of chemically converting a cytosine (C) to a uracil (U) without chemically modifying a methylated cytosine and therefore can be used to differentially modify a DNA sequence based on the methylation status of the DNA.

As used herein, a reagent that "differentially modifies" methylated or non-methylated DNA encompasses any reagent that reacts differentially with methylated and unmethylated DNA in a process through which distinguishable products or quantitatively distinguishable results (e.g. degree of binding or precipitation) are generated from methylated and non-methylated DNA, thereby allowing the identification of the DNA methylation status. Such processes may include, but are not limited to, chemical reactions (such as an unmethylated C→U conversion by bisulfite), enzymatic treatment (such as cleavage by a methylation-dependent endonuclease), binding, and precipitation. Thus, an enzyme that preferentially cleaves methylated DNA is one capable of cleaving a DNA molecule at a much higher efficiency when the DNA is methylated, whereas an enzyme that preferentially cleaves unmethylated DNA exhibits a significantly higher efficiency when the DNA is not methylated. In the context of the present invention, a reagent that "differentially modifies" methylated and unmethylated DNA also refers to any reagent that exhibits differential ability in its binding to DNA sequences or precipitation of DNA sequences depending on their methylation status. One class of such reagents consists of methylated DNA binding proteins.

A "CpG-containing genomic sequence" as used herein refers to a segment of DNA sequence at a defined location in the genome of an individual. Typically, a "CpG-containing genomic sequence" is at least 15 contiguous nucleotides in length and contains at least one CpG pair. In some cases, it can be at least 18, 20, 25, 30, 50, 80, 100, 150, 200, 250, or 300 contiguous nucleotides in length and contains at least 2, 3, 4, 5, 6, 7, 8, 9, 10, 15, 20, 25, or 30 CpG pairs. For any one "CpG-containing genomic sequence" at a given location, e.g., within a region of the human BCL6B genomic sequence (such as the region containing the promoter and exon 1), nucleotide sequence variations may exist from individual to individual and from allele to allele even for the same individual. Furthermore, a "CpG-containing genomic sequence" may encompass a nucleotide sequence transcribed or not transcribed for protein production, and the nucleotide sequence can be a protein-coding sequence, a non protein-coding sequence (such as a transcription promoter), or a combination thereof.

The term "immunoglobulin" or "antibody" (used interchangeably herein) refers to an antigen-binding protein having a basic four-polypeptide chain structure consisting of two heavy and two light chains, said chains being stabilized, for example, by interchain disulfide bonds, which has the ability to specifically bind antigen. Both heavy and light chains are folded into domains.

The term "antibody" also refers to antigen- and epitope-binding fragments of antibodies, e.g., Fab fragments, that can be used in immunological affinity assays. There are a number of well characterized antibody fragments. Thus, for example, pepsin digests an antibody C-terminal to the disulfide linkages in the hinge region to produce F(ab)'$_2$, a dimer of Fab which itself is a light chain joined to $V_H$-$C_H$1 by a disulfide bond. The F(ab)'$_2$ can be reduced under mild conditions to break the disulfide linkage in the hinge region thereby converting the (Fab')$_2$ dimer into an Fab' monomer. The Fab' monomer is essentially a Fab with part of the hinge region (see, e.g., Fundamental Immunology, Paul, ed., Raven Press, N.Y. (1993), for a more detailed description of other antibody fragments). While various antibody fragments are defined in terms of the digestion of an intact antibody, one of skill will appreciate that fragments can be synthesized de novo either chemically or by utilizing recombinant DNA methodology. Thus, the term antibody also includes antibody fragments either produced by the modification of whole antibodies or synthesized using recombinant DNA methodologies.

The phrase "specifically binds," when used in the context of describing a binding relationship of a particular molecule to a protein or peptide, refers to a binding reaction that is determinative of the presence of the protein in a heterogeneous population of proteins and other biologics. Thus, under designated binding assay conditions, the specified binding agent (e.g., an antibody) binds to a particular protein at least two times the background and does not substantially bind in a significant amount to other proteins present in the sample. Specific binding of an antibody under such conditions may require an antibody that is selected for its specificity for a particular protein or a protein but not its similar "sister" proteins. A variety of immunoassay formats may be used to select antibodies specifically immunoreactive with a particular protein or in a particular form. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity). Typically a specific or selective binding reaction will be at least twice background signal or noise and more typically more than 10 to 100 times background. On the other hand, the term "specifically bind" when used in the context of referring to a polynucleotide sequence forming a double-stranded complex with another polynucleotide sequence describes "polynucleotide hybridization" based on the Watson-Crick base-pairing, as provided in the definition for the term "polynucleotide hybridization method."

As used in this application, an "increase" or a "decrease" refers to a detectable positive or negative change in quantity from a comparison control, e.g., an established standard control (such as an average expression level of BCL6B mRNA or protein found in non-cancerous stomach tissue). An increase is a positive change that is typically at least 10%, or at least 20%, or 50%, or 100%, and can be as high as at least 2-fold or at least 5-fold or even 10-fold of the control value. Similarly, a decrease is a negative change that is typically at least 10%, or at least 20%, 30%, or 50%, or even as high as at least 80% or 90% of the control value. Other terms indicating quantitative changes or differences from a comparative basis, such as "more," "less," "higher," and "lower," are used in this application in the same fashion as described above. In contrast, the term "substantially the same" or "substantially lack of change" indicates little to no change in quantity from the standard control value, typically within ±10% of the standard control, or within ±5%, 2%, or even less variation from the standard control.

A "polynucleotide hybridization method" as used herein refers to a method for detecting the presence and/or quantity of a pre-determined polynucleotide sequence based on its ability to form Watson-Crick base-pairing, under appropriate hybridization conditions, with a polynucleotide probe of a known sequence. Examples of such hybridization methods include Southern blot, Northern blot, and in situ hybridization.

"Primers" as used herein refer to oligonucleotides that can be used in an amplification method, such as a polymerase chain reaction (PCR), to amplify a nucleotide sequence based on the polynucleotide sequence corresponding to a gene of interest, e.g., the cDNA or genomic sequence for human BCL6B or a portion thereof. Typically at least one of the PCR primers for amplification of a polynucleotide sequence is sequence-specific for that polynucleotide sequence. The exact length of the primer will depend upon many factors, including temperature, source of the primer, and the method used. For example, for diagnostic and prognostic applications, depending on the complexity of the target sequence, the oligonucleotide primer typically contains at least 10, or 15, or 20, or 25 or more nucleotides, although it may contain fewer nucleotides or more nucleotides. The factors involved in determining the appropriate length of primer are readily known to one of ordinary skill in the art. The primers used in particular embodiments are shown in Table 1 of the disclosure where their specific applications are indicated. In this disclosure the term "primer pair" means a pair of primers that hybridize to opposite strands a target DNA molecule or to regions of the target DNA which flank a nucleotide sequence to be amplified. In this disclosure the term "primer site", means the area of the target DNA or other nucleic acid to which a primer hybridizes.

A "label," "detectable label," or "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins that can be made detectable, e.g., by incorporating a radioactive component into the peptide or used to detect antibodies specifically reactive with the peptide. Typically a detectable label is attached to a probe or a molecule with defined binding characteristics (e.g., a polypeptide with a known binding specificity or a polynucleotide), so as to allow the presence of the probe (and therefore its binding target) to be readily detectable.

"Standard control" as used herein refers to a predetermined amount or concentration of a polynucleotide sequence or polypeptide, e.g., BCL6B mRNA or protein, that is present in an established normal disease-free tissue sample, e.g., a normal stomach epithelial tissue sample. The standard control value is suitable for the use of a method of the present invention, to serve as a basis for comparing the amount of BCL6B mRNA or protein that is present in a test sample. An established sample serving as a standard control provides an average amount of BCL6B mRNA or protein that is typical for a stomach epithelial tissue sample (e.g., stomach mucosa) of an average, healthy human without any stomach disease especially gastric cancer as conventionally defined. A standard control value may vary depending on the nature of the sample as well as other factors such as the gender, age, ethnicity of the subjects based on whom such a control value is established.

The term "average," as used in the context of describing a human who is healthy, free of any stomach disease (especially gastric cancer) as conventionally defined, refers to certain characteristics, especially the amount of human BCL6B mRNA or BCL6B protein, found in the person's stomach tissue, e.g., epithelial tissue or gastric mucosa, that are representative of a randomly selected group of healthy humans who are free of any stomach diseases (especially gastric cancer). This selected group should comprise a sufficient number of humans such that the average amount of BCL6B mRNA or protein in the stomach mucosa among these individuals reflects, with reasonable accuracy, the corresponding amount of BCL6B mRNA/protein in the general population of healthy humans. In addition, the selected group of humans generally have a similar age to that of a subject whose stomach tissue sample is tested for indication of gastric cancer. Moreover, other factors such as gender, ethnicity, medical history are also considered and preferably closely matching between the profiles of the test subject and the selected group of individuals establishing the "average" value.

The term "amount" as used in this application refers to the quantity of a polynucleotide of interest or a polypeptide of interest, e.g., human BCL6B mRNA or protein, present in a sample. Such quantity may be expressed in the absolute terms, i.e., the total quantity of the polynucleotide or polypeptide in the sample, or in the relative terms, i.e., the concentration of the polynucleotide or polypeptide in the sample.

The term "treat" or "treating," as used in this application, describes an act that leads to the elimination, reduction, alleviation, reversal, or prevention or delay of onset or recurrence of any symptom of a relevant condition. In other words, "treating" a condition encompasses both therapeutic and prophylactic intervention against the condition.

The term "effective amount" as used herein refers to an amount of a given substance that is sufficient in quantity to produce a desired effect. For example, an effective amount of an polynucleotide encoding BCL6B mRNA is the amount of said polynucleotide to achieve an increased level of BCL6B protein expression or biological activity, such that the symptoms of gastric cancer are reduced, reversed, eliminated, prevented, or delayed of the onset in a patient who has been given the polynucleotide for therapeutic purposes. An amount adequate to accomplish this is defined as the "therapeutically effective dose." The dosing range varies with the nature of the therapeutic agent being administered and other factors such as the route of administration and the severity of a patient's condition.

The term "subject" or "subject in need of treatment," as used herein, includes individuals who seek medical attention due to risk of, or actual suffering from, gastric cancer. Subjects also include individuals currently undergoing therapy that seek manipulation of the therapeutic regimen. Subjects or individuals in need of treatment include those that demonstrate symptoms of gastric cancer or are at risk of suffering from gastric cancer or its symptoms. For example, a subject in need of treatment includes individuals with a genetic predisposition or family history for gastric cancer, those that have suffered relevant symptoms in the past, those that have been exposed to a triggering substance or event, as well as those suffering from chronic or acute symptoms of the condition. A "subject in need of treatment" may be at any age of life.

"Inhibitors," "activators," and "modulators" of BCL6B protein are used to refer to inhibitory, activating, or modulating molecules, respectively, identified using in vitro and in vivo assays for BCL6B protein binding or signaling, e.g., ligands, agonists, antagonists, and their homologs and mimetics. The term "modulator" includes inhibitors and activators Inhibitors are agents that, e.g., partially or totally block carbohydrate binding, decrease, prevent, delay activation, inactivate, desensitize, or down regulate the activity of BCL6B protein. In some cases, the inhibitor directly or indirectly binds to BCL6B protein, such as a neutralizing antibody. Inhibitors, as used herein, are synonymous with inactivators and antagonists. Activators are agents that, e.g., stimulate, increase, facilitate, enhance activation, sensitize or up regulate the activity of BCL6B protein. Modulators include BCL6B protein ligands or binding partners, including modifications of naturally-occurring ligands and synthetically-designed ligands, antibodies and antibody fragments, antagonists, agonists, small molecules including carbohydrate-containing molecules, siRNAs, RNA aptamers, and the like.

DETAILED DESCRIPTION OF THE INVENTION

I. Introduction

Gastric cancer patients often face a grim prognosis due to the nature of this disease in its lacking of specific symptoms during its early development stages. Early detection of gastric cancer is therefore critical for improving patient survival rate.

The present inventors discovered for the first time that expression of BCL6B protein is suppressed in gastric cancer cells. This suppressed expression of BCL6B protein is due to increased methylation in the BCL6B genomic sequence, especially in the promoter region of the gene, which leads to decreased transcription of BCL6B mRNA. This discovery provides important means for detecting, monitoring, and treating gastric cancer.

II. General Methodology

Practicing this invention utilizes routine techniques in the field of molecular biology. Basic texts disclosing the general methods of use in this invention include Sambrook and Russell, *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Protein sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage and Caruthers, *Tetrahedron Lett.* 22:1859-1862 (1981), using an automated synthesizer, as described in Van Devanter et. al., *Nucleic Acids Res.* 12:6159-6168 (1984). Purification of oligonucleotides is performed using any art-recognized strategy, e.g., native acrylamide gel electrophoresis or anion-exchange high performance liquid chromatography (HPLC) as described in Pearson and Reanier, *J. Chrom.* 255: 137-149 (1983).

The sequence of interest used in this invention, e.g., the polynucleotide sequence of the human BCL6B gene, and synthetic oligonucleotides (e.g., primers) can be verified using, e.g., the chain termination method for sequencing double-stranded templates of Wallace et al., *Gene* 16: 21-26 (1981).

III. Acquisition of Tissue Samples and Analysis of BCL6B mRNA or DNA

The present invention relates to measuring the amount of BCL6B mRNA or analyzing the methylation pattern of BCL6B genomic DNA found in a person's stomach tissue, especially stomach epithelial sample, as a means to detect the presence, to assess the risk of developing, and/or to monitor the progression or treatment efficacy of gastric cancer. Thus, the first steps of practicing this invention are to obtain a stomach epithelial tissue sample from a test subject and extract mRNA or DNA from the sample.

A. Acquisition and Preparation of Stomach Tissue Samples

A stomach tissue sample is obtained from a person to be tested or monitored for gastric cancer using a method of the present invention. Collection of stomach epithelial tissue sample from an individual is performed in accordance with the standard protocol hospitals or clinics generally follow, such as during an endoscopy. An appropriate amount of stomach epithelium is collected and may be stored according to standard procedures prior to further preparation.

The analysis of BCL6B mRNA or DNA found in a patient's stomach epithelial sample according to the present invention may be performed using, e.g., stomach mucosa. The methods for preparing tissue samples for nucleic acid extraction are well known among those of skill in the art. For example, a subject's stomach mucosa sample should be first treated to disrupt cellular membrane so as to release nucleic acids contained within the cells.

B. Extraction and Quantitation of RNA

There are numerous methods for extracting mRNA from a biological sample. The general methods of mRNA preparation (e.g., described by Sambrook and Russell, *Molecular Cloning: A Laboratory Manual* 3d ed., 2001) can be followed; various commercially available reagents or kits, such as Trizol reagent (Invitrogen, Carlsbad, Calif.), Oligotex Direct mRNA Kits (Qiagen, Valencia, Calif.), RNeasy Mini Kits (Qiagen, Hilden, Germany), and PolyATtract® Series 9600™ (Promega, Madison, Wis.), may also be used to obtain mRNA from a biological sample from a test subject. Combinations of more than one of these methods may also be used.

It is essential that all contaminating DNA be eliminated from the RNA preparations. Thus, careful handling of the samples, thorough treatment with DNase, and proper negative controls in the amplification and quantification steps should be used.

1. PCR-Based Quantitative Determination of mRNA Level

Once mRNA is extracted from a sample, the amount of human BCL6B mRNA may be quantified. The preferred method for determining the mRNA level is an amplification-based method, e.g., by polymerase chain reaction (PCR), especially reverse transcription-polymerase chain reaction (RT-PCR).

Prior to the amplification step, a DNA copy (cDNA) of the human BCL6B mRNA must be synthesized. This is achieved by reverse transcription, which can be carried out as a separate step, or in a homogeneous reverse transcription-polymerase chain reaction (RT-PCR), a modification of the polymerase chain reaction for amplifying RNA. Methods suitable for PCR amplification of ribonucleic acids are described by Romero and Rotbart in *Diagnostic Molecular Biology: Principles and Applications* pp. 401-406; Persing et al., eds., Mayo Foundation, Rochester, Minn., 1993; Egger et al., *J. Clin. Microbiol.* 33:1442-1447, 1995; and U.S. Pat. No. 5,075,212.

The general methods of PCR are well known in the art and are thus not described in detail herein. For a review of PCR methods, protocols, and principles in designing primers, see, e.g., Innis, et al., *PCR Protocols: A Guide to Methods and Applications*, Academic Press, Inc. N.Y., 1990. PCR reagents and protocols are also available from commercial vendors, such as Roche Molecular Systems.

PCR is most usually carried out as an automated process with a thermostable enzyme. In this process, the temperature of the reaction mixture is cycled through a denaturing region, a primer annealing region, and an extension reaction region automatically. Machines specifically adapted for this purpose are commercially available.

Although PCR amplification of the target mRNA is typically used in practicing the present invention. One of skill in the art will recognize, however, that amplification of these mRNA species in a maternal blood sample may be accomplished by any known method, such as ligase chain reaction (LCR), transcription-mediated amplification, and self-sustained sequence replication or nucleic acid sequence-based amplification (NASBA), each of which provides sufficient amplification. More recently developed branched-DNA technology may also be used to quantitatively determining the amount of mRNA markers in maternal blood. For a review of branched-DNA signal amplification for direct quantitation of nucleic acid sequences in clinical samples, see Nolte, *Adv. Clin. Chem.* 33:201-235, 1998.

2. Other Quantitative Methods

The BCL6B mRNA can also be detected using other standard techniques, well known to those of skill in the art. Although the detection step is typically preceded by an amplification step, amplification is not required in the methods of the invention. For instance, the mRNA may be identified by size fractionation (e.g., gel electrophoresis), whether or not proceeded by an amplification step. After running a sample in an agarose or polyacrylamide gel and labeling with ethidium bromide according to well known techniques (see, e.g., Sambrook and Russell, supra), the presence of a band of the same size as the standard comparison is an indication of the presence of a target mRNA, the amount of which may then be compared to the control based on the intensity of the band. Alternatively, oligonucleotide probes specific to BCL6B mRNA can be used to detect the presence of such mRNA species and indicate the amount of mRNA in comparison to the standard comparison, based on the intensity of signal imparted by the probe.

Sequence-specific probe hybridization is a well known method of detecting a particular nucleic acid comprising other species of nucleic acids. Under sufficiently stringent hybridization conditions, the probes hybridize specifically only to substantially complementary sequences. The stringency of the hybridization conditions can be relaxed to tolerate varying amounts of sequence mismatch.

A number of hybridization formats well known in the art, including but not limited to, solution phase, solid phase, or mixed phase hybridization assays. The following articles provide an overview of the various hybridization assay formats: Singer et al., *Biotechniques* 4:230, 1986; Haase et al., *Methods in Virology*, pp. 189-226, 1984; Wilkinson, *In situ Hybridization*, Wilkinson ed., IRL Press, Oxford University Press, Oxford; and Hames and Higgins eds., *Nucleic Acid Hybridization: A Practical Approach*, IRL Press, 1987.

The hybridization complexes are detected according to well known techniques. Nucleic acid probes capable of specifically hybridizing to a target nucleic acid, i.e., the mRNA or the amplified DNA, can be labeled by any one of several methods typically used to detect the presence of hybridized nucleic acids. One common method of detection is the use of autoradiography using probes labeled with $^3$H, $^{125}$I, $^{35}$S, $^{14}$C, or $^{32}$P, or the like. The choice of radioactive isotope depends on research preferences due to ease of synthesis, stability, and half lives of the selected isotopes. Other labels include compounds (e.g., biotin and digoxigenin), which bind to antiligands or antibodies labeled with fluorophores, chemiluminescent agents, and enzymes. Alternatively, probes can be conjugated directly with labels such as fluorophores, chemiluminescent agents or enzymes. The choice of label depends on sensitivity required, ease of conjugation with the probe, stability requirements, and available instrumentation.

The probes and primers necessary for practicing the present invention can be synthesized and labeled using well known techniques. Oligonucleotides used as probes and primers may be chemically synthesized according to the solid phase phosphoramidite triester method first described by Beaucage and Caruthers, *Tetrahedron Letts.*, 22:1859-1862, 1981, using an automated synthesizer, as described in Needham-VanDevanter et al., *Nucleic Acids Res.* 12:6159-6168, 1984. Purification of oligonucleotides is by either native acrylamide gel electrophoresis or by anion-exchange HPLC as described in Pearson and Regnier, *J. Chrom.*, 255: 137-149, 1983.

C. Detection of Methylation in BCL6B Genomic Sequence

Methylation status of a segment of BCL6B genomic sequence containing one or more CpG (cytosine-guanine dinucleotide) pairs is investigated to provide indication as to whether a test subject is suffering from gastric cancer, whether the subject is at risk of developing gastric cancer, or whether the subject's gastric cancer is worsening or improving.

Typically a segment of the BCL6B genomic sequence that includes the 5' untranslated region (such as the promoter region) and includes one or more CpG nucleotide pairs is analyzed for methylation pattern. For example, SEQ ID NO:9, 18, or 19 or a portion thereof can be used to determine how many of the CpG pairs within the sequence are methylated and how many are not methylated. The sequence being analyzed should be long enough to contain at least 1 CpG dinucleotide pair and detection of methylation at this CpG site is typically adequate indication of the presence of gastric cancer cells. The length of the sequence being analyzed is usually at least 15 or 20 contiguous nucleotides, and may be longer with at least 25, 30, 50, 100, 200, 300, 400, or more contiguous nucleotides. At least one, typically 2 or more, often 3, 4, 5, 6, 7, 8, 9, or more, CpG nucleotide pairs are present within the sequence. In the cases of multiple (2 or more) CpG sites are analyzed for methylation status, when at least 50% of the CpG pairs within the analyzed genomic sequence are shown to be methylated, subject being tested is deemed to have gastric cancer or have an elevated risk of developing gastric cancer. As an example, SEQ ID NO:19, a segment of BCL6B genomic sequence (−72 to +49 in relation to the transcription start site) shown in FIG. 8 and FIG. 9, contains 9 CpG pairs. As illustrated in these figures, majority of the CpG pairs in this region are found to be methylated in established gastric cancer cell lines and samples taken from gastric cancer, whereas non-cancerous stomach epithelial cells showed very few, if any at all, methylated CpG sites. For the purpose of determining the methylation pattern of a BCL6B genomic sequence, bisulfite treatment followed by DNA sequencing is particularly useful, since bisulfite converts an unmethylated cytosine (C) to a uracil (U) while leaving methylated cytosines unchanged, allowing immediate identification through a DNA sequencing process. Optionally, an amplification process such as PCR is included after the bisulfite conversion and before the DNA sequencing.

1. DNA Extraction and Treatment

Methods for extracting DNA from a biological sample are well known and routinely practiced in the art of molecular biology, see, e.g., Sambrook and Russell, supra. RNA contamination should be eliminated to avoid interference with DNA analysis. The DNA is then treated with a reagent capable of modifying DNA in a methylation differential manner, i.e., different and distinguishable chemical structures will result from a methylated cytosine (C) residue and an unmethylated C residue following the treatment. Typically, such a reagent reacts with the unmethylated C residue(s) in a DNA molecule and converts each unmethylated C residue to a uracil (U) residue, whereas the methylated C residues remain unchanged. This unmethylated C→U conversion allows detection and comparison of methylation status based on changes in the primary sequence of the nucleic acid. An exemplary reagent suitable for this purpose is bisulfite, such as sodium bisulfite. Methods for using bisulfite for chemical modification of DNA are well known in the art (see, e.g., Herman et al., *Proc. Natl. Acad. Sci. USA* 93:9821-9826, 1996).

As a skilled artisan will recognize, any other reagents that are unnamed here but have the same property of chemically (or through any other mechanism) modifying methylated and unmethylated DNA differentially can be used for practicing the present invention. For instance, methylation-specific modification of DNA may also be accomplished by methylation-sensitive restriction enzymes, some of which typically cleave an unmethylated DNA fragment but not a methylated DNA fragment, while others (e.g., methylation-dependent endonuclease McrBC) cleave DNA containing methylated cytosines but not unmethylated DNA. In addition, a combination of chemical modification and restriction enzyme treatment, e.g., combined bisulfite restriction analysis (COBRA) (Xiong et al. 1997 *Nucleic Acids Res.* 25(12): 2532-2534), is useful for practicing the present invention. Other available methods for detecting DNA methylation include, for example, methylation-sensitive restriction endonucleases (MSREs) assay by either Southern blot or PCR analysis, methylation specific or methylation sensitive-PCR (MS-PCR), methylation-sensitive single nucleotide primer extension (Ms-SnuPE), high resolution melting (HRM) analysis, bisulifte sequencing, pyrosequencing, methylation-specific single-strand conformation analysis (MS-SSCA), methylation-specific denaturing gradient gel electrophoresis (MS-DGGE), methylation-specific melting curve analysis (MS-MCA), methylation-specific denaturing high-performance liquid chromatography (MS-DHPLC), methylation-specific microarray (MSO). These assays can be either PCR analysis, quantitative analysis with fluorescence labelling or Southern blot analysis. Exemplary methylation sensitive DNA cleaving reagent such as restriction enzymes include AatII, AciI, AclI, AgeI, AscI, Asp718, AvaI, BbrP1, BceAI, BmgBI, BsaAI, BsaHI, BsiEI, BsiWI, BsmBI, BspDI, BsrFI, BssHII, BstBI, BstUI, ClaI, EagI, EagI-HF™, FauI, FseI, FspI, HaeII, HgaI, HhaI, HinP1I, HpaII, Hpy99I, HpyCH4IV, KasI, MluI, NarI, NgoMIV, NotI, NotI-HF™, NruI, Nt.BsmAI, PaeR7I, PspXI, PvuI, RsrII, SacII, SalI, SalI-HF™, SfoI, SgrAI, SmaI, SnaBI or TspMI.

2. Optional Amplification and Sequence Analysis

Following the modification of DNA in a methylation-differential manner, the treated DNA is then subjected to sequence-based analysis, such that the methylation status of the BCL6B genomic sequence may be determined. An amplification reaction is optional prior to the sequence analysis after methylation specific modification. A variety of polynucleotide amplification methods are well established and frequently used in research. For instance, the general methods of polymerase chain reaction (PCR) for polynucleotide sequence amplification are well known in the art and are thus not described in detail herein. For a review of PCR methods, protocols, and principles in designing primers, see, e.g., Innis, et al., *PCR Protocols: A Guide to Methods and Applications*, Academic Press, Inc. N.Y., 1990. PCR reagents and protocols are also available from commercial vendors, such as Roche Molecular Systems.

Although PCR amplification is typically used in practicing the present invention, one of skill in the art will recognize that amplification of the relevant genomic sequence may be accomplished by any known method, such as the ligase chain reaction (LCR), transcription-mediated amplification, and self-sustained sequence replication or nucleic acid sequence-based amplification (NASBA), each of which provides sufficient amplification.

Techniques for polynucleotide sequence determination are also well established and widely practiced in the relevant research field. For instance, the basic principles and general techniques for polynucleotide sequencing are described in various research reports and treatises on molecular biology and recombinant genetics, such as Wallace et al., supra; Sambrook and Russell, supra, and Ausubel et al., supra. DNA sequencing methods routinely practiced in research laboratories, either manual or automated, can be used for practicing the present invention. Additional means suitable for detecting changes (e.g., C→U) in a polynucleotide sequence for practicing the methods of the present invention include but are not limited to mass spectrometry, primer extension, polynucleotide hybridization, real-time PCR, melting curve analysis, high resolution melting analysis, heteroduplex analysis, pyrosequencing, and electrophoresis.

IV. Quantitation of Polypeptides

A. Obtaining Samples

The first step of practicing the present invention is to obtain a sample of stomach epithelium from a subject being tested, assessed, or monitored for gastric cancer, the risk of developing gastric cancer, or the severity/progression of the condition. Samples of the same type should be taken from both a control group (normal individuals not suffering from any stomach disorder especially neoplasia) and a test group (subjects being tested for possible gastric cancer, for example). Standard procedures routinely employed in hospitals or clinics are typically followed for this purpose, as stated in the previous section.

For the purpose of detecting the presence of gastric cancer or assessing the risk of developing gastric cancer in test subjects, individual patients' stomach mucosa samples may be taken and the level of human BCL6B protein may be measured and then compared to a standard control. If a decrease in the level of human BCL6B protein is observed when compared to the control level, the test subject is deemed to have gastric cancer or have an elevated risk of developing the condition. For the purpose of monitoring disease progression or assessing therapeutic effectiveness in gastric cancer patients, individual patient's stomach epithelial samples may be taken at different time points, such that the level of human BCL6B protein can be measured to provide information indicating the state of disease. For instance, when a patient's BCL6B protein level shows a general trend of increase over time, the patient is deemed to be improving in the severity of gastric cancer or the therapy the patient has been receiving is deemed effective. A lack of change in a patient's BCL6B protein level or a continuing trend of decrease on other hand would indicate a worsening of the condition and ineffectiveness of the therapy given to the patient. Generally, a lower BCL6B protein level seen in a patient indicates a more severe form of the gastric cancer the patient is suffering from and a worse prognosis of the disease, as manifested in shorter life expectancy, higher rate of metastasis, resistance to therapy etc.

B. Preparing Samples for BCL6B Protein Detection

The stomach tissue sample from a subject is suitable for the present invention and can be obtained by well known methods and as described in the previous section. In certain applications of this invention, stomach mucosa may be the preferred sample type.

C. Determining the Level of Human BCL6B Protein

A protein of any particular identity, such as BCL6B protein, can be detected using a variety of immunological assays. In some embodiments, a sandwich assay can be performed by capturing the polypeptide from a test sample with an antibody having specific binding affinity for the polypeptide. The polypeptide then can be detected with a labeled antibody having specific binding affinity for it. Such immunological assays can be carried out using microfluidic devices such as microarray protein chips. A protein of interest (e.g., human BCL6B protein) can also be detected by gel electrophoresis (such as 2-dimensional gel electrophoresis) and western blot analysis using specific antibodies. Alternatively, standard immunohistochemical techniques can be used to detect a given protein (e.g., human BCL6B protein), using the appropriate antibodies. Both monoclonal and polyclonal antibodies (including antibody fragment with desired binding specificity) can be used for specific detection of the polypeptide. Such antibodies and their binding fragments with specific binding affinity to a particular protein (e.g., human BCL6B protein) can be generated by known techniques.

Other methods may also be employed for measuring the level of BCL6B protein in practicing the present invention. For instance, a variety of methods have been developed based on the mass spectrometry technology to rapidly and accurately quantify target proteins even in a large number of samples. These methods involve highly sophisticated equipment such as the triple quadrupole (triple Q) instrument using the multiple reaction monitoring (MRM) technique, matrix assisted laser desorption/ionization time-of-flight tandem mass spectrometer (MALDI TOF/TOF), an ion trap instrument using selective ion monitoring SIM) mode, and the electrospray ionization (ESI) based QTOP mass spectrometer. See, e.g., Pan et al., *J Proteome Res.* 2009 February; 8(2):787-797.

V. Establishing a Standard Control

In order to establish a standard control for practicing the method of this invention, a group of healthy persons free of any stomach disease (especially any form of tumor such as gastric cancer) as conventionally defined is first selected. These individuals are within the appropriate parameters, if applicable, for the purpose of screening for and/or monitoring gastric cancer using the methods of the present invention. Optionally, the individuals are of same gender, similar age, or similar ethnic background.

The healthy status of the selected individuals is confirmed by well established, routinely employed methods including but not limited to general physical examination of the individuals and general review of their medical history.

Furthermore, the selected group of healthy individuals must be of a reasonable size, such that the average amount/concentration of human BCL6B mRNA or BCL6B protein in the stomach tissue sample obtained from the group can be reasonably regarded as representative of the normal or average level among the general population of healthy people. Preferably, the selected group comprises at least 10 human subjects.

Once an average value for the BCL6B mRNA or BCL6B protein is established based on the individual values found in each subject of the selected healthy control group, this average or median or representative value or profile is considered a standard control. A standard deviation is also determined during the same process. In some cases, separate standard controls may be established for separately defined groups having distinct characteristics such as age, gender, or ethnic background.

VI. Treatment of Gastric Cancer

By illustrating the correlation of suppressed expression of BCL6B protein and gastric cancer, the present invention further provides a means for treating patients suffering from gastric cancer: by way of increasing BCL6B protein expression or biological activity. As used herein, treatment of gastric cancer encompasses reducing, reversing, lessening, or eliminating one or more of the symptoms of gastric cancer, as well as preventing or delaying the onset of one or more of the relevant symptoms.

A. Increasing BCL6B Expression or Activity

1. Nucleic Acids Encoding BCL6B Proteins

Enhancement of BCL6B gene expression can be achieved through the use of nucleic acids encoding a functional BCL6B protein. Such nucleic acids can be single-stranded nucleic acids (such as mRNA) or double-stranded nucleic acids (such as DNA) that can translate into an active form of BCL6B protein under favorable conditions.

In one embodiment, the BCL6B-encoding nucleic acid is provided in the form of an expression cassette, typically recombinantly produced, having a promoter operably linked to the polynucleotide sequence encoding the BCL6B protein. In some cases, the promoter is a universal promoter that directs gene expression in all or most tissue types; in other cases, the promoter is one that directs gene expression specifically in epithelial cells, especially in stomach epithelium. Administration of such nucleic acids can increase the BCL6B protein expression in the target tissue, e.g., stomach epithelium. Since the human BCL6B gene sequence is known as GenBank Accession No. NM_181844.3 and provided herein as SEQ ID NO:11, one can derive a suitable BCL6B-encoding nucleic acid from the sequence, species homologs, and variants of these sequences.

2. BCL6B Proteins

By directly administering an effective amount of an active BCL6B protein to a patient suffering from gastric cancer and exhibiting suppressed BCL6B protein expression or activity, the disease may also be effectively treated. For example, this can be achieved by administering a recombinantly produced BCL6B protein possessing its biological activity to the patient suffering from gastric cancer. Formulations and methods for delivering a protein- or polypeptide-based therapeutic agent are well known in the art.

3. Activators of BCL6B Protein

Increased BCL6B protein activity can be achieved with an agent that is capable of activating the expression of BCL6B protein or enhancing the activity of BCL6B protein. For example, a demethylating agent (e.g., 5-Aza) may be able to activate BCL6B gene expression by removing the suppression of BCL6B gene expression caused by methylation of the promoter region of this gene. Other activating agents may include transcriptional activators specific for the BCL6B promoter and/or enhancer. Such activating agents can be screened for and identified using the BCL6B expression assays described in the examples herein.

Agonists of the BCL6B protein, such as an activating antibody, are another kind of activators of the BCL6B protein. Such activators act by enhancing the biological activity of the BCL6B protein, typically (but not necessarily) by direct binding with the BCL6B protein and/or its interacting proteins. Preliminary screening for such agonists may start with a binding assay for identifying molecules that physically interact with BCL6B protein.

B. Pharmaceutical Compositions

1. Formulations

Compounds of the present invention are useful in the manufacture of a pharmaceutical composition or a medicament. A pharmaceutical composition or medicament can be administered to a subject for the treatment of gastric cancer.

Compounds used in the present invention, e.g., a BCL6B protein, a nucleic acid encoding BCL6B protein, or an activator of BCL6B gene expression, are useful in the manufacture of a pharmaceutical composition or a medicament comprising an effective amount thereof in conjunction or mixture with excipients or carriers suitable for application.

An exemplary pharmaceutical composition for enhancing BCL6B expression comprises (i) an express cassette comprising a polynucleotide sequence encoding a human BCL6B protein as described herein, and (ii) a pharmaceutically acceptable excipient or carrier. The terms pharmaceutically-acceptable and physiologically-acceptable are used synonymously herein. The expression cassette may be provided in a therapeutically effective dose for use in a method for treatment as described herein.

A BCL6B protein or a nucleic acid encoding a BCL6B protein can be administered via liposomes, which serve to target the conjugates to a particular tissue, as well as increase the half-life of the composition. Liposomes include emulsions, foams, micelles, insoluble monolayers, liquid crystals, phospholipid dispersions, lamellar layers and the like. In these preparations the inhibitor to be delivered is incorporated as part of a liposome, alone or in conjunction with a molecule which binds to, e.g., a receptor prevalent among the targeted cells (e.g., skin cells), or with other therapeutic or immunogenic compositions. Thus, liposomes filled with a desired inhibitor of the invention can be directed to the site of treatment, where the liposomes then deliver the selected inhibitor compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka et al. (1980) *Ann. Rev. Biophys. Bioeng.* 9: 467, U.S. Pat. Nos. 4,235,871, 4,501,728 and 4,837,028.

Pharmaceutical compositions or medicaments for use in the present invention can be formulated by standard techniques using one or more physiologically acceptable carriers or excipients. Suitable pharmaceutical carriers are described herein and in "Remington's Pharmaceutical Sciences" by E. W. Martin. Compounds and agents of the present invention and their physiologically acceptable salts and solvates can be formulated for administration by any suitable route, including via inhalation, topically, nasally, orally, parenterally, or rectally.

Typical formulations for topical administration include creams, ointments, sprays, lotions, and patches. The pharmaceutical composition can, however, be formulated for any type of administration, e.g., intradermal, subdermal, intravenous, intramuscular, intranasal, intracerebral, intratracheal, intraarterial, intraperitoneal, intravesical, intrapleural, intracoronary or intratumoral injection, with a syringe or other devices. Formulation for administration by inhalation (e.g., aerosol), or for oral, rectal, or vaginal administration is also contemplated.

2. Routes of Administration

Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Suitable formulations for transdermal application include an effective amount of a compound or agent of the present invention with carrier. Preferred carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used.

For oral administration, a pharmaceutical composition or a medicament can take the form of, for example, a tablet or a capsule prepared by conventional means with a pharmaceutically acceptable excipient. Preferred are tablets and gelatin capsules comprising the active ingredient, i.e., a BCL6B protein or a nucleic acid encoding a BCL6B protein, together with (a) diluents or fillers, e.g., lactose, dextrose, sucrose, mannitol, sorbitol, cellulose (e.g., ethyl cellulose, microcrystalline cellulose), glycine, pectin, polyacrylates and/or calcium hydrogen phosphate, calcium sulfate, (b) lubricants, e.g., silica, talcum, stearic acid, its magnesium or calcium salt, metallic stearates, colloidal silicon dioxide, hydrogenated vegetable oil, corn starch, sodium benzoate, sodium acetate and/or polyethyleneglycol; for tablets also (c) binders, e.g., magnesium aluminum silicate, starch paste, gelatin, tragacanth, methylcellulose, sodium carboxymethylcellulose, polyvinylpyrrolidone and/or hydroxypropyl methylcellulose; if desired (d) disintegrants, e.g., starches (e.g., potato starch or sodium starch), glycolate, agar, alginic acid or its sodium salt, or effervescent mixtures; (e) wetting agents, e.g., sodium lauryl sulphate, and/or (f) absorbents, colorants, flavors and sweeteners.

Tablets may be either film coated or enteric coated according to methods known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

Compounds and agents of the present invention can be formulated for parenteral administration by injection, for example by bolus injection or continuous infusion. Formulations for injection can be presented in unit dosage form, for example, in ampoules or in multi-dose containers, with an added preservative. Injectable compositions are preferably aqueous isotonic solutions or suspensions, and suppositories are preferably prepared from fatty emulsions or suspensions. The compositions may be sterilized and/or contain adjuvants, such as preserving, stabilizing, wetting or emulsifying agents, solution promoters, salts for regulating the osmotic pressure and/or buffers. Alternatively, the active ingredient can be in powder form for constitution with a suitable vehicle, for example, sterile pyrogen-free water, before use. In addition, they may also contain other therapeutically valuable substances. The compositions are prepared according to conventional mixing, granulating or coating methods, respectively, and contain about 0.1 to 75%, preferably about 1 to 50%, of the active ingredient.

For administration by inhalation, the active ingredient, e.g., a BCL6B protein or a nucleic acid encoding a BCL6B protein, may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch.

The inhibitors can also be formulated in rectal compositions, for example, suppositories or retention enemas, for example, containing conventional suppository bases, for example, cocoa butter or other glycerides.

Furthermore, the active ingredient can be formulated as a depot preparation. Such long-acting formulations can be administered by implantation (for example, subcutaneously or intramuscularly) or by intramuscular injection. Thus, for example, the active ingredient can be formulated with suitable polymeric or hydrophobic materials (for example as an emulsion in an acceptable oil) or ion exchange resins, or as sparingly soluble derivatives, for example, as a sparingly soluble salt.

A pharmaceutical composition or medicament of the present invention comprises (i) an effective amount of a compound as described herein that increases the level or activity of BCL6B protein, and (ii) another therapeutic agent. When used with a compound of the present invention, such therapeutic agent may be used individually, sequentially, or in combination with one or more other such therapeutic agents (e.g., a first therapeutic agent, a second therapeutic agent, and a compound of the present invention). Administration may be by the same or different route of administration or together in the same pharmaceutical formulation.

3. Dosage

Pharmaceutical compositions or medicaments can be administered to a subject at a therapeutically effective dose to prevent, treat, or control gastric cancer as described herein. The pharmaceutical composition or medicament is administered to a subject in an amount sufficient to elicit an effective therapeutic response in the subject.

The dosage of active agents administered is dependent on the subject's body weight, age, individual condition, surface area or volume of the area to be treated and on the form of administration. The size of the dose also will be determined by the existence, nature, and extent of any adverse effects that accompany the administration of a particular compound in a particular subject. For example, each type of BCL6B protein or nucleic acid encoding a BCL6B protein will likely have a unique dosage. A unit dosage for oral administration to a mammal of about 50 to 70 kg may contain between about 5 and 500 mg of the active ingredient. Typically, a dosage of the active compounds of the present invention, is a dosage that is sufficient to achieve the desired effect. Optimal dosing schedules can be calculated from measurements of agent accumulation in the body of a subject. In general, dosage may be given once or more daily, weekly, or monthly. Persons of ordinary skill in the art can easily determine optimum dosages, dosing methodologies and repetition rates.

To achieve the desired therapeutic effect, compounds or agents may be administered for multiple days at the therapeutically effective daily dose. Thus, therapeutically effective administration of compounds to treat a pertinent condition or disease described herein in a subject requires periodic (e.g., daily) administration that continues for a period ranging from three days to two weeks or longer. Typically, agents will be administered for at least three consecutive days, often for at least five consecutive days, more often for at least ten, and sometimes for 20, 30, 40 or more consecutive days. While consecutive daily doses are a preferred route to achieve a therapeutically effective dose, a therapeutically beneficial effect can be achieved even if the agents are not administered daily, so long as the administration is repeated frequently enough to maintain a therapeutically effective concentration of the agents in the subject. For example, one can administer the agents every other day, every third day, or, if higher dose ranges are employed and tolerated by the subject, once a week.

Optimum dosages, toxicity, and therapeutic efficacy of such compounds or agents may vary depending on the relative potency of individual compounds or agents and can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Agents that exhibit large therapeutic indices are preferred. While agents that exhibit toxic side effects can be used, care should be taken to design a delivery system that targets such agents to the site of affected tissue to minimize potential damage to normal cells and, thereby, reduce side effects.

The data obtained from, for example, cell culture assays and animal studies can be used to formulate a dosage range for use in humans. The dosage of such compounds lies preferably within a range of circulating concentrations that include the $ED_{50}$ with little or no toxicity. The dosage can vary within this range depending upon the dosage form employed and the route of administration. For any agents used in the methods of the invention, the therapeutically effective dose can be estimated initially from cell culture assays. A dose can be formulated in animal models to achieve a circulating plasma concentration range that includes the $IC_{50}$ (the concentration of the agent that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of agents is from about 1 ng/kg to 100 mg/kg for a typical subject.

Exemplary dosages for BCL6B protein or a nucleic acid encoding a BCL6B protein described herein are provided. Dosage for a BCL6B-encoding nucleic acid, such as an expression cassetter, can be between 0.1-0.5 mg/eye, with intravitreous administration (e.g., 5-30 mg/kg). Small organic compounds activators can be administered orally at between 5-1000 mg, or by intravenous infusion at between 10-500 mg/ml. Monoclonal antibody activators can be administered by intravenous injection or infusion at 50-500 mg/ml (over 120 minutes); 1-500 mg/kg (over 60 minutes); or 1-100 mg/kg (bolus) five times weekly. BCL6B Protein or peptide activators can be administered subcutaneously at 10-500 mg; 0.1-500 mg/kg intravenously twice daily, or about 50 mg once weekly, or 25 mg twice weekly.

Pharmaceutical compositions of the present invention can be administered alone or in combination with at least one additional therapeutic compound. Exemplary advantageous therapeutic compounds include systemic and topical anti-inflammatories, pain relievers, anti-histamines, anesthetic compounds, and the like. The additional therapeutic compound can be administered at the same time as, or even in the same composition with, main active ingredient (e.g., a BCL6B protein or a nucleic acid encoding the protein). The additional therapeutic compound can also be administered separately, in a separate composition, or a different dosage form from the main active ingredient. Some doses of the main ingredient, such as a BCL6B protein or a nucleic acid encoding a BCL6B protein, can be administered at the same time as the additional therapeutic compound, while others are administered separately, depending on the particular symptoms and characteristics of the individual.

The dosage of a pharmaceutical composition of the invention can be adjusted throughout treatment, depending on severity of symptoms, frequency of recurrence, and physiological response to the therapeutic regimen. Those of skill in the art commonly engage in such adjustments in therapeutic regimen.

VII. Kits and Devices

The invention provides compositions and kits for practicing the methods described herein to assess the level of BCL6B mRNA or BCL6B protein in a subject, which can be used for various purposes such as detecting or diagnosing the presence of gastric cancer, determining the risk of developing gastric cancer, and monitoring the progression of gastric cancer in a patient.

Kits for carrying out assays for determining BCL6B mRNA level typically include at least one oligonucleotide useful for specific hybridization with at least one segment of the BCL6B coding sequence or its complementary sequence. Optionally, this oligonucleotide is labeled with a detectable moiety. In some cases, the kits may include at least two oligonucleotide primers that can be used in the amplification of at least one segment of BCL6B DNA or mRNA by PCR, particularly by RT-PCR.

Kits for carrying out assays for determining BCL6B protein level typically include at least one antibody useful for specific binding to the BCL6B protein amino acid sequence. Optionally, this antibody is labeled with a detectable moiety. The antibody can be either a monoclonal antibody or a polyclonal antibody. In some cases, the kits may include at least two different antibodies, one for specific binding to the BCL6B protein (i.e., the primary antibody) and the other for detection of the primary antibody (i.e., the secondary antibody), which is often attached to a detectable moiety.

Typically, the kits also include an appropriate standard control. The standard controls indicate the average value of BCL6B protein or BCL6B mRNA in the stomach epithelium of healthy subjects not suffering from gastric cancer. In some cases such standard control may be provided in the form of a set value. In addition, the kits of this invention may provide instruction manuals to guide users in analyzing test samples and assessing the presence, risk, or state of gastric cancer in a test subject.

In a further aspect, the present invention can also be embodied in a device or a system comprising one or more such devices, which is capable of carrying out all or some of the method steps described herein. For instance, in some cases, the device or system performs the following steps upon receiving a stomach tissue sample, e.g., a stomach mucosa sample taken from a subject being tested for detecting gastric cancer, assessing the risk of developing gastric cancer, or monitored for progression of the condition: (a) determining in sample the amount or concentration of BCL6B mRNA, BCL6B protein; (b) comparing the amount or concentration with a standard control value; and (c) providing an output indicating whether gastric cancer is present in the subject or whether the subject is at risk of developing gastric cancer, or whether there is a change, i.e., worsening or improvement, in the subject's gastric cancer condition. In other cases, the device or system of the invention performs the task of steps (b) and (c), after step (a) has been performed and the amount or concentration from (a) has been entered into the device. Preferably, the device or system is partially or fully automated.

EXAMPLES

The following examples are provided by way of illustration only and not by way of limitation. Those of skill in the art will readily recognize a variety of non-critical parameters that could be changed or modified to yield essentially the same or similar results.

Materials and Methods
Human Gastric Specimens
Tissue Samples

Paired biopsy specimens from gastric primary tumor and adjacent nontumor sites were obtained from 12 gastric cancer patients during endoscopy in the Prince of Wales Hospital, the Chinese University of Hong Kong, before any therapeutic intervention. These samples were used in the BCL6B gene expression level comparison.

Two cohorts of patients with confirmed gastric adenocarcinoma were examined to evaluate the clinical significance of BCL6B methylation status in gastric cancer (GC) patients. The first cohort (cohort I) included 208 patients diagnosed in the First Affiliated Hospital, Sun Yat-sen University, Guangzhou, whereas 101 members of the second cohort (cohort II) were diagnosed in the Prince of Wales Hospital, the Chinese University of Hong Kong. Cohort II was used to further validate the findings in cohort I. Cohort I included 127 male and 81 female, with average age 57.2±12.7, and cohort II included 55 male and 46 female, with average age 65.6±12.9. Other clinicopathologic features such as *Helicobacter pylori* (*H. pylori*) infection, TNM stages and differentiation status were also determined. By using rapid urease test (RUT), 43 patients were found infected by *H. pylori*, and 98 patients were *H. pylori* infection negative in cohort I, while 30 patients were positive, and 32 patients were negative in cohort II. The patient number in TNM stage I, II, III and IV were 30, 31, 62 and 72 in cohort I, while the number in the four stage were 15, 17, 29 and 28 in cohort II, respectively. There were 122, 39 patients with low differentiation GC, and 57, 31 patients had developed moderate or high differentiation GC in cohort I, while the number is 39 and 31 in cohort II, respectively. Some of the information was not complete. All tumor tissues were obtained from patients at the time of operation. In addition, 20 samples of normal gastric mucosa were included as controls, which were also obtained from the Prince of Wales Hospital, the Chinese University of Hong Kong.

The specimens were snap-frozen in liquid nitrogen and stored at −80° C. for molecular analyses. The remaining tissue specimens were fixed in 10% formalin and embedded in paraffin for routine histologic examination. All subjects provided informed consent for obtaining the study specimens. The study protocol was approved by the Ethics Committee of the Chinese University of Hong Kong.

Tumor Cell Line

Nine gastric cancer cell lines (AGS, BGC823, Kato III, MGC803, MKN28, MKN45, SNU1, SNU16 and SNU719) were used in this study. Cell lines were maintained in RPMI-1640 medium (Gibco BRL, Rockville, Md.) with 10% fetal bovine serum (Gibco BRL). All these cell lines were incubated in an incubator with 95% air and 5% $CO_2$ at 37° C. Culture media were renewed every two to four days. Cells were split at 1:3~1:4 ratio using 0.25% Trypsin-EDTA solution (Invitrogen, Carlsbad, Calif., USA).

Bioinformatics Analysis of BCL6B Gene

The online database of University of California Santa Cruz Genome Bioinformatics (UCSC) (website: genome.ucsc.edu) was used to obtain the related information about BCL6B gene.

CpG islands in the BCL6B gene promoter region were predicted by CpG Island Searcher (website: cpgislands.usc.edu; Takai and Jones, *In Silico Biol.*, 3(3), 235-240, 2003). CpG islands are defined as DNA region greater than 500 bp with GC content above 55% and an observed/expected CpG ratio above 0.65 (Takai and Jones, *PNAS*, 99(6), 3740-3745, 2002). The foregoing methods and tools will be readily apparent to those skilled in the art.

Gene Expression Analysis

RNA Isolation

Total RNA was isolated using Quizol reagent (Qiagen, Valencia, Calif., USA). First, about 5–10×10$^6$ cells or 30 mg tissue was homogenized in 1 mL Qiazol reagent and incubated at room temperature for 10 min. For each sample, 0.2 mL chloroform was added. The mixture should be shaken vigorously for 15 sec and placed at room temperature for another 3 min. Samples were centrifuged at 12,000 g for 20 min at 4° C. and separated into two layers. The upper aqueous phase containing RNA was transferred to a new tube, mixed with 0.7 ml isopropanol, incubated at room temperature for 10 min and then centrifuged at 12,000 g for 10 min at 4° C. After discarding the supernatant, the RNA pellet was washed twice with 1 mL 75% ethanol; air dried for 5 min and re-dissolved the RNA with RNase-free $H_2O$. Contamination of DNA was eliminated by the RNase-free DNaseI digestion (GE Healthcare, Buckinghamshire, England). The quality and quantity of total RNA were determined by measuring absorbance at 260 nm/280 nm using NanoDrop ND-1000 (NanoDrop Technologies, Wilmington, Del., USA). The purified RNA was store at −80° C. until using.

cDNA synthesis

MultiScribe Reverse Transcriptase Kit (Applied Biosystems, Foster City, Calif., USA) was used to synthesize cDNA. The reaction mixture contained 1×Reverse Transcriptase buffer, 1×dNTP, 1×random primer (supplied by kit), 2.5 U/μL reverse transcriptase, 1 U/μL RNase inhibitor and 2 μg total RNA. The mixture was incubated at 25° C. for 10 min, then 37° C. for 120 min, then 85° C. 5 min to inactivate the enzymes. The cDNA was stored at −80° C. until other application.

Semiquantitative Reverse Transcription PCR(RT-PCR)

Semiquantitative RT-PCR was performed in a total volume of 25 μL reaction containing GeneAmp 1×PCR Buffer II (Applied Biosystems), 2.5 mM $MgCl_2$, 200 μM each of dNTP, 200 nM each of primers, 0.5 U of AmpliTaq Gold DNA polymerase (Applied Biosystems) and 30~50 ng cDNA. The PCR program started with an initial denaturation at 95° C. for 10 min, followed by 32-35 cycles (94° C. for 30 sec, 58° C. for 30 sec, and 72° C. for 30 sec) of amplification, with a final extension at 72° C. for 10 min. The PCR bands were visualized under ultraviolet light and photographed. The expression of the target gene was normalized by the expression of house keeping gene β-actin, which served as an internal control. All primers used to amplify the transcripts are listed in Table 1.

Protein Extraction

Protein was prepared by using CytoBuster Protein Extraction Reagent (Merck Chemicals, Nottingham, UK). The cells were pelleted at 3000 g for 10 min. Then the pellet was resuspended in CytoBuster using 100 μL per 10$^6$ cells. The mixture was incubated at room temperature for 5 min. Then centrifuge the tube for 10 min at 4° C. at 15,000 g and transfer the supernatant to a fresh tube.

Sodium Dodecyl Sulfate Polyacrylamide Gel Electrophoresis (SDS-PAGE) and Western Blot Forty micrograms of protein were separated by 5% upper gel and 10% lower gel. After SDS-PAGE, the protein was transfer to an equilibrated polyvinylidene difluoride (PVDF) membrane (Amersham Biosciences, Buckinghamshire, UK) by semi-dry machine at 15 V for 40 min. The membrane was blocked in 5% non-fat milk dissolved by TBS/T solution (Tris-buffered saline (Invitrogen) and 0.1% Tween 20 (Sigma-Aldrich)) at room temperature for 1 hr with shaking After blocking, the membrane was incubated in primary antibody diluted in 5% non-fat milk at 4° C. overnight with shaking. After incubation with the secondary antibody at room temperature for 1 hr, the proteins were detected by enhanced chemiluminescence (ECL, Amersham Corporation, Arlington. Heights, Ill., USA).

DNA Methylation Analysis

Genomic DNA Extraction

Genomic DNA from GC cell lines and tissue samples were isolated by using DNA mini kit (Qiagen) according to the kit protocol. About 25 mg samples were lysed in 180 μL of QIAamp ATL buffer and 20 μL of proteinase K in a 1.5 mL microcentrifuge tubes for 1 hour at 56° C. Four microliter of RNase A (100 mg/ml, QIAgen) was added and mixed by pulse-vortexing for 15 s followed by 2 min incubation at room temperature. Then 200 μL of AL buffer was added to the lysate and samples were incubated for 10 min at 70° C. After adding 200 μL of absolute ethanol, the solution was mixed by pulse-vortexing for 15 s. Then lysates were purified over a QIAamp column as specified by the manufacturer. The genomic DNA was diluted in 200 μL DNase-free $H_2O$. The quality and quantity of DNA were determined by measuring absorbance at 260 nm/280 nm using NanoDrop ND-1000 (NanoDrop).

Sodium Bisulfite Conversion

The genomic DNA was modified by sodium metabisulfite as description by Tao et al., *Hum. Mol. Genet.*, 11(18):2091-2101, 2002. Briefly, 5 μg genomic DNA in 30 μL TE buffer (Sigma-Aldrich) was mixed with 3.3 μL of 3 mM NaOH to a final concentration of 0.3 mM and incubate at 37° C. for 15 min. Denatured DNA was mixed with 333 μL of bisulfite solution and treated in darkness for 4 hr at 55° C. The bisulfite solution was prepared as 2.4 M sodium metabisulfite (pH 5.0-5.2) (Sigma-Aldrich) and 0.5 mM hydroquinone (Sigma-Aldrich). The treated DNA was desalted and purified using the Qiaex II kit (Qiagen) according to the protocol supplied by the kit. DNA was then treated with 0.3 M NaOH at 37° C. for 15 min and precipitated with 3 M ammonium acetate and 3 volumes of ethanol. Recovered DNA was dissolved in 100 μL TE buffer (pH 8.0) and stored at −20° C.

Demethylation Treatment Using 5-aza-2'-deoxycytidine ("5-Aza")

Cells were seeded at a density of $1\times10^5$/100-mm dishes and grew for 24 hr. Cells were then treated with 2 μM 5-aza-2'-deoxycytidine ("5-Aza") (Sigma-Aldrich) for 5 days. The 5-Aza was replenished every day. The gene expression of BCL6B was evaluated using semiquantitative RT-PCR.

Methylation Specific PCR (MSP)

Methylation specific and unmethylation specific primers were designed to assess methylation status in the GC cell lines. The mixture for PCR contained 1×PCR Buffer II (Applied Biosystems), 2 mM $MgCl_2$, 200 μM each of dNTP, 600 nM each of primers, 0.5 U of AmpliTaq Gold DNA polymerase (Applied Biosystems) and 20 ng bisulfite treated DNA. The PCR program was 95° C. for 10 min, followed by 38 cycles (94° C. for 30 sec, 60° C. for 30 sec, and 72° C. for 30 sec) of amplification, with a final extension at 72° C. for 5 min. Bands of MSP were observed under ultraviolet light and photographed.

Combined Bisulfite Restriction Analysis (COBRA)

Combined bisulfite restriction analysis is a technique to semiquantitate the methylated and unmethylated DNA after sodium bisulfite modification by using restriction enzyme cutting sites. PCR amplification with 2 μL of bisulfite-treated DNA gives a PCR product of 190 bp, encompassing the BCL6B promoter region −95 to +95 bp relative to the transcription start site (SEQ ID NO:18). This region contained 9 CpG dinucleotides and 1 BstUI restriction sites. The PCR products were digested with BstUI (New England Biolabs, Ipswich, Mass.) that had C only within CpG sites in its recognition sequence. BstUI cleaved the sequence 5'-CGCG-3', which was retained in the bisulfite-treated methylated DNA, but not in the unmethylated DNA. The DNA digests were separated in nondenaturing polyacrylamide gels and stained with ethidium bromide. COBRA was used to profile methylation status in GC cell lines, normal stomach and GC samples.

Bisulfite Genomic Sequencing (BGS)

Bisulfite treated DNA was amplified with primers for COBRA. The PCR products were cloned into the pCR4-Topo vector (Invitrogen, Carlsbad, Calif.), with seven to eight colonies randomly chosen and sequenced. Sequencing analysis was performed by SeqScape software (Applied Biosystems, Foster City, Calif.).

Biological Function Analysis

Cloning of BCL6B and Construction of Expression Vector

The full-length cDNA of BCL6B gene expression vector was generated by PCR-cloning. Total RNA from human stomach (Ambion, Austin, Tex., USA) was reverse transcribed into cDNA. Sequence corresponding to the open reading frame (ORF) of BCL6B was amplified by PCR. PCR product was subcloned into the pCDNA3.1 TOPO TA expression vector according to the manufacturer's guideline (Invitrogen). Briefly, 1 μL, PCR product was ligated into the 0.5 μL TOPO vector in a total volume of 2.5 μL, containing 240 mM NaCl and 12 mM $MgCl_2$. The mixed reaction was incubated for 30 min at room temperature before heat shock transformation.

The heat-shock transformation was performed using JM109 chemically competent *Escherichia coli* (*E. coli*) cell (Promega, Madison, Wis., USA). The JM109 competent cells (50 μL) were thawed on ice, and 2 μL, of ligation product was added into the cells. After incubation on ice for 20 min, the cells were heated shock for 45 sec at 42° C. without shaking in a water bath and then immediately transferred the tube on ice for 5 min. S.O.C. medium (250 μL) was added to the cells and the tube was shaken at 220 rpm at 37° C. for 1 hr in a shaking incubator. After incubation, 150 μL, cells were spread on Luria-Bertani (LB) agar plates containing 0.1 mg/ml ampicillin and incubated overnight at 37° C.

Bacterial colonies were identified by PCR. Positive colonies were cultured in LB medium with 0.1 mg/ml ampicillin. Insert DNA was checked by sequencing. Plasmids with non-mutation target gene were isolated using HiSpeed Plasmid Maxi Kit (Qiagen). Briefly, bacterial were cultured in 1 mL LB medium containing 0.1 mg/ml ampicillin at 37° C. overnight with shaking at 250 rpm. Then, 0.5 mL bacterial culture was further inoculated into 100 mL LB medium containing 0.1 mg/ml ampicillin and grew at 37° C. for 16 hr with shaking at 250 rpm. Bacterial pellet was harvested by centrifugation at 6000 g for 15 min at 4° C. The pellet was resuspended in 10 mL Buffer P1. Bacterial protein, chromosomal and plasmid DNA were denatured with 10 mL Buffer P2. The tube was inverted upside down for six times and then placed at room temperature for 5 min. The mixture was neutralized with 10 mL Buffer P3, followed by incubation at room temperature for 10 min. Debris within the cell lysate was cleared by filtrating with the QIAfilter cartridge. The filtrated lysate was applied to the resin column supplied in the kit through gravity flow, and plasmid DNA was bound to the resin column. The column was washed with 30 mL QC buffer by gravity flow to remove all contaminants during plasmid preparations and carbohydrates from bacterial strains. Plasmid DNA was eluted with 15 mL Buffer QF. DNA was precipitated by isopropanol precipitation and the DNA pellet was washed with 70% ethanol. The DNA pellet was air-dried and dissolved with 1 mL DNase-free $H_2O$.

BCL6B Gene Transfection

Cells were seeded at $1\times10^4$~$2.5\times10^4$ cells on a 24-well plate without antibiotics for about 24 hr till the cell density reached about 90% confluent. Cells were then transfected with 0.8 μg BCL6B and control vector (pCDNA3.1) respectively using Lipofectamine 2000 (Invitrogen). Lipofectamine 2000 (2.0 μL) diluted in 50 μL Opti-MEM (Invitrogen) was incubate at room temperature for 5 min. Then, plasmid DNA diluted in 50 μL Opti-MEM was combined with the Lipofectamine mixture. After 24~48 hr incubation at 37° C. in a 5% $CO_2$ incubator, cells were harvested for testing of transgenic expression. For stable cell lines, cells were passaged at a 1:10 ratio into fresh growth medium with proper concentration of neomycin (G418) (Invitrogen). Stable transfection cells were harvested after 14-21 days of selection for functional assays.

Colony Formation Assay

Two days after transfection, cells were subsequently split at 1:20 ratio on six-well plates with RPMI1640 in 10% FBS containing 500 µg/mL neomycin (G418). After 14-18 days of selection, cells were fixed with 70% ethanol for 10 min and stained with 0.5% crystal violet solution for 10 min. Colony with more than 50 cells per colony was counted. The experiment was conducted in three independent triplicates.

Cell Viability Assay

MTS assay, which is the short form of 3-(4,5-dimethylthiazol-2-yl)-5-(3-carboxymethoxyphenyl)-2-(4-sulfophenyl)-2H-tetrazolium assay, was performed using CellTiter 96 $AQ_{ueous}$ One Solution Cell Proliferation Assay kit (Promega). Transfected cells were trypsinized and counted. Cells were diluted to 5,000 cells per 100 µL in RPMI1640 medium. For each well in the 96-well plate, 100 µL of cells were seeded. The plate was incubated at 37° C. in a 5% $CO_2$ incubator. After 48 hr, 20 µL MTS reagent was added into the culture medium. The culture was incubated at 37° C. in a $CO_2$ incubator for 30 min to 2 hr. Absorbance of the samples was measured at 490 nm 48 hr post transfection. This experiment was replicated three times.

Annexin V Apoptosis Assay

Annexin V is a protein which could bind the cell membrane after apoptosis have occurred and before membrane integrity has been lost. The proportion of apoptotic cells was evaluated using Annexin V and 7-amino-actinomycin (7-AAD) double staining Briefly, the cells washed with 1×PBS was resuspended in 100 µL ice-cold annexin-binding buffer (10 mM HEPES, 140 mM NaCl and 2.5 mM CaCl2, pH 7.4) containing 5 µL Annexin V conjugated with Alexa Fluor 488 (Invitrogen) and 2 µL 7-AAD staining. After incubation for 15 min at room temperature, cells were mixed with additional 400 µL of ice-cold annexin-binding buffer and analyzed using flow cytometry.

In Vivo Tumorigenicity

BGC823 cells ($1 \times 10^7$ cells in 0.1 mL PBS) transfected with pCDNA3.1-BCL6B or pCDNA3.1 only were injected subcutaneously into the dorsal left flank of 5-week-old male Balb/c nude mice, separately. After tumors were visible, the tumor size was measured every 2 days until 3 weeks. Tumor volume ($mm^3$) was estimated by measuring the longest and shortest diameter of the tumor and calculating as follows: volume=(shortest diameter)$^2$×(longest diameter)×0.5. Care of animals and all experimental procedures were approved by the Animal Ethics Committee of the Chinese University of Hong Kong. After 3 weeks, the mice were sacrificed, and the tumors were weighed and fixed in formalin for histological analysis.

Immunohistochemistry

Immunohistochemistry (IHC) was performed on the paired paraffin sections after deparaffinization. Peroxidase quenching with 3% $H_2O_2$ in PBS was performed to sections. Sections were then washed in water and preblocked with normal goat serum for 10 min. In primary antibody reaction, sections were incubated with anti-BCL6B antibodies (Abcam) for 1 h at room temperature. The sections were then incubated with biotinylated secondary antibodies (1:400) for 45 min. Following a washing step with PBS, the avidin-biotin complex (Strept ABComplex; DAKO, CA) was applied.

Statistical Analysis

Mann-Whitney U test was performed to compare the difference of BCL6B protein expression between tumor and adjacent nontumor tissues. Independent samples t-test was performed to analyze statistical significant difference between control and BCL6B over-expressed cells in colony formation, MTS assay, annexin V and 7-AAD double staining assay and tumor weight in nude mice. The chi-square test was employed for analysis of patient features. Kaplan-Meier survival curve and log-rank test were used to evaluate overall survival data corresponding to BCL6B methylation status. The difference in tumor growth rate between the 2 groups of mice stably transfected with BCL6B expression vector and control vector was determined by repeated measures analysis of variance (ANOVA). Data were considered statistically significant when P is less than 0.05; and very significant when P is less than 0.01.

Results

Data Mining for BCL6B Gene

BCL6B

BCL6B is a homolog of B-cell CLL/lymphoma 6 (BCL6) and acts as a sequence-specific transcriptional repressor. Using University of California Santa Cruz Genome Bioinformatics (UCSC) database, the present inventors obtained the information that BCL6B gene was located at chromosome 17p13.1. BCL6B encodes a transcription repressor which has 480 amino acids.

BCL6B CpG Island

Using CpG Island Searcher, a CpG island was identified spanning the promoter region and the first exon: GC content, 63%; observed/expected CpG ratio, 0.668; 58 CpG sites in a 902 bp region (SEQ ID NO:20). The MSP primers and COBRA/BGS primers were designed according to the CpG island analysis result (FIG. 1 and Table 1). FIG. 1 shows part of the promoter region and the first exon of BCL6B. Transcription starting site is marked as TSS. The COBRA/BGS region and the 9 CpG sites within the COBRA/BGS region are also presented.

BCL6B Gene Expression

BCL6B is Expressed in Most of Human Tissues

To determine the expression profile of BCL6B, the BCL6B expression level was examined in human normal tissues. Using semi-quantitative RT-PCR, the inventors found BCL6B expressed in most of the human tissues, especially in digestion organs like liver, spleen, pancreas, stomach, small intestine, colon, and rectum.

BCL6B is Epigenetically Suppressed in Cancer Cell Lines

Figure 2:
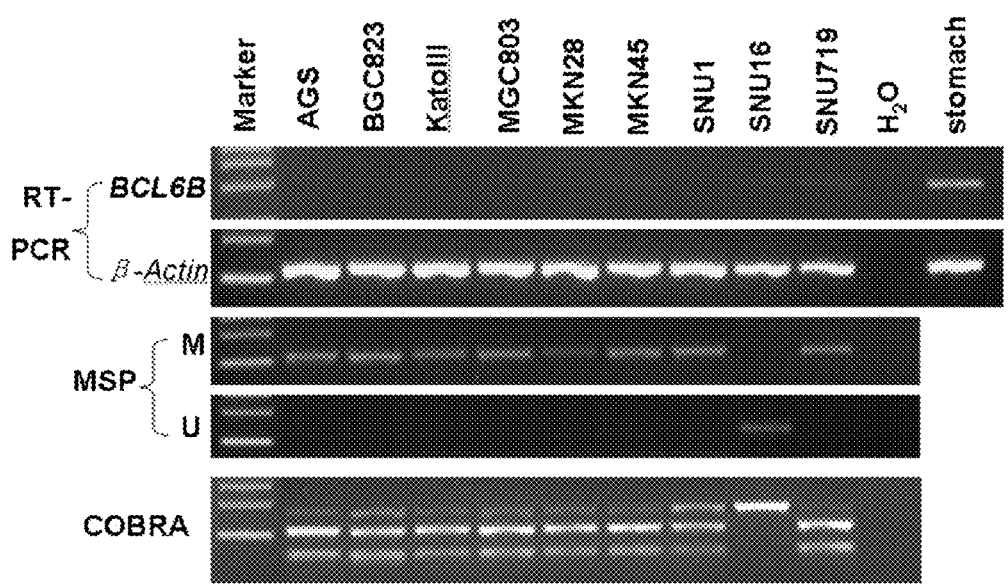
FIG. 2 shows BCL6B mRNA expression in cell lines in an embodiment.

To characterize epigenetic effectors of BCL6B in GC, expression level and methylation status of BCL6B gene in 9 GC cell lines were examined. FIG. 2 shows BCL6B mRNA expression and promoter methylation in GC cell lines. The mRNA expression of BCL6B in cell lines was determined by RT-PCR. Amplification of β-Actin was performed as an internal control for RNA quality. MSP and COBRA was performed to detect the methylation status. (M: bands amplified by methylation primers, U: bands amplified by unmethylation primers)

BCL6B gene was reduced or silenced in 9 (100%) cell lines, but was readily expressed in the normal stomach tissue (FIG. 2).

To assess whether the silence or down-regulation of BCL6B could match the methylation status of the promoter region, MSP and COBRA was performed using methylation specific primers and unmethylation specific primers. MSP amplicon covered the region of −59 bp~+48 bp relative to translation start (the DNA sequence of this region is shown in SEQ ID NO:9). Full or partial methylation was detected in 8 GC cell lines (AGS, BGC823, KatoIII, MGC803, MKN28, MKN45, SNU1 and SNU719). The methylation status in GC cell lines matched the expression level well except for SNU16 cell line, in which BCL6B was silenced but no methylation was detected. It is possible that BCL6B gene in SNU16 is silenced by other mechanisms such as histone modification or up-steam transcriptional regulation.

BCL6B Expression could be Restored after Demethylation Treatment

Figure 3:
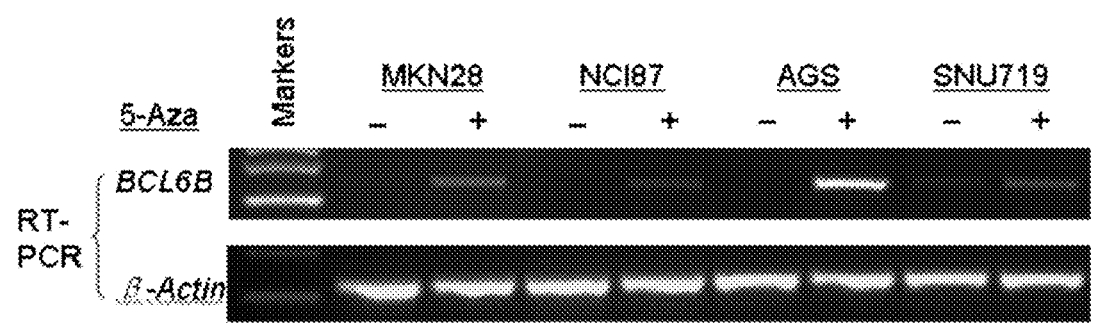
FIG. 3 shows the effect of a demethylating agent on BCL6B expression in an embodiment.

To confirm that BCL6B expression was repressed by promoter methylation, 5-Aza was used to pharmacologically interfere with promoter methylation in methylated cell lines of AGS, MKN28, NCI87 and SNU719. FIG. 3 shows BCL6B gene expression in 5-Aza demethylation treated GC cell lines as determined by RT-PCR. As shown in FIG. 3, 5-Aza treatment could restore expression of all these cell lines, conferring promoter methylation contributes to the epigenetic suppression of BCL6B in GC cell lines.

BCL6B Expression in Paired Cancer and Adjacent Normal Samples

Figure 4:
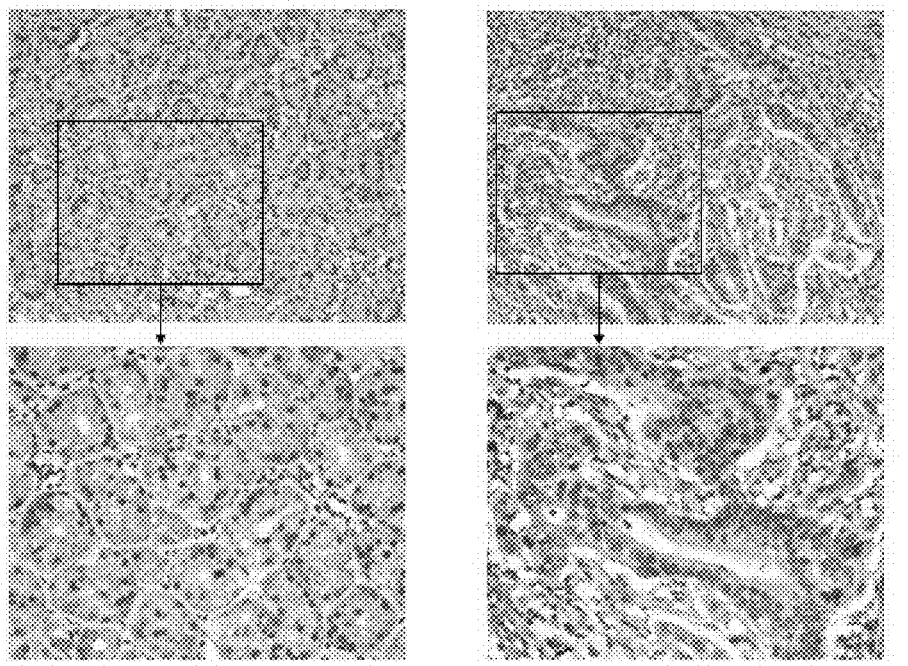
FIG. 4 shows the relative protein expression level of BCL6B in paired samples of gastric cancer cells and adjacent normal tissues in an embodiment.
Figure 4:
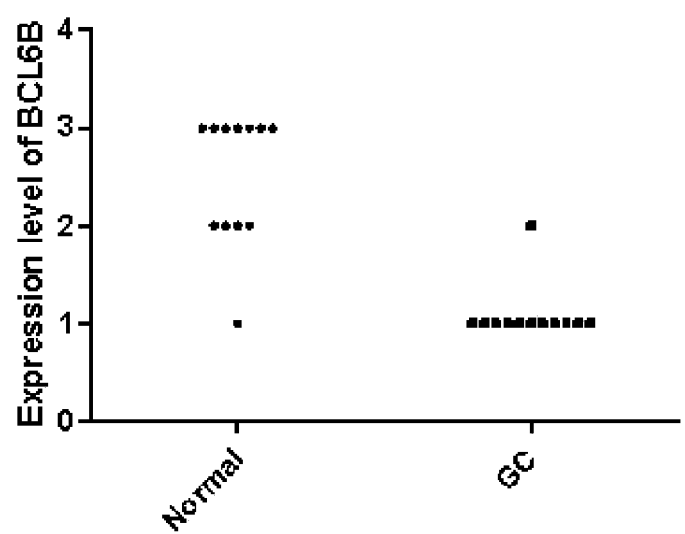

To evaluate the clinical significance of BCL6B gene in primary tumors, the inventors compared the protein expression level of BCL6B in 12 pairs of GC biopsies and their adjacent non-tumor tissues using immunohistochemistry (IHC). The extent of BCL6B staining was scored from 1 (less than 20% of positive staining cells) to 3 (more than 50% of positive staining cells) and the scoring was performed blindly by two independent investigators, whose estimates correlated well. BCL6B protein was found to be down-regulated significantly in primary tumor specimens as compared with the adjacent nontumor tissues (P<0.001, FIGS. 4A and 4B).

Functional Assay

Inhibition of Cell Proliferation by BCL6B

Figure 5:
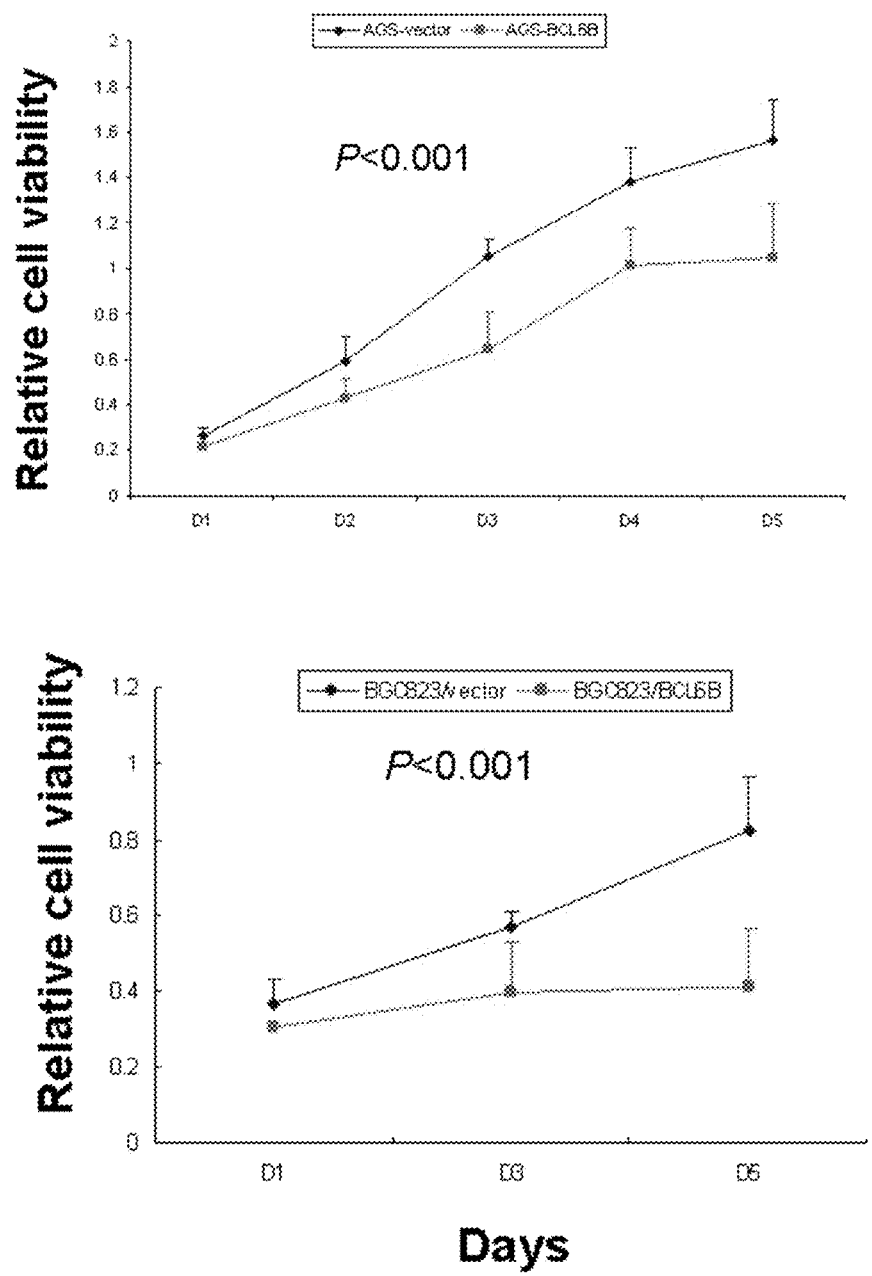
FIG. 5 shows exogenous BCL6B expression on cells in MTS assay in an embodiment.
Figure 6:
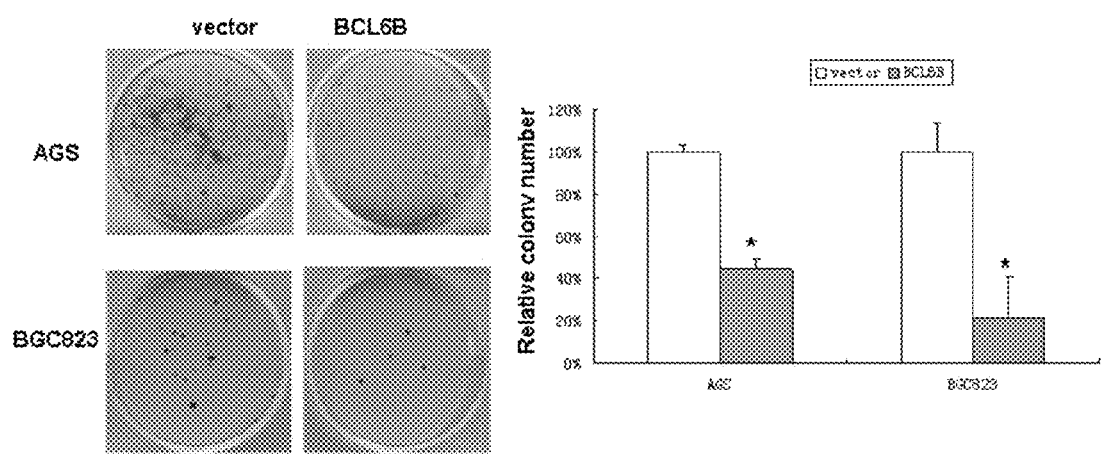
FIG. 6 shows the effect of BCL6B expression on transfected cells in Colony formation assay in an embodiment.

In vitro biological effects of BCL6B on cell growth in the BCL6B non-expressing cell lines (AGS and BGC823) were examined by cell viability assay and colony formation assay. MTS assay was used for measuring the cell viability. Ectopic expression of BCL6B in these GC cell lines caused a significant decrease in cell viability (FIG. 5). The inhibitory effect on GC cell growth was further confirmed by colony formation assay. The colonies formed in BCL6B-transfected cells were significantly lesser and smaller in size than in empty vector-transfected cells (down to 22%-44% of vector control, P<0.01) (FIG. 6). Both colony formation and MTS assay solidly demonstrated that BCL6B could inhibit cell growth of GC cells in vitro.

Induction of Cell Apoptosis by BCL6B

To examine the contribution of apoptosis to the observed growth inhibition of BCL6B-transfected cells, cell apoptosis was determined by flow cytometry with Annexin V and 7-AAD double staining.

The results indicated an increase in the numbers of both early apoptotic cells (13.14%±0.65% vs. 6.58%±0.52%, P<0.001) and late apoptotic cells (5.82%±0.63% vs. 4.30%±0.16%, P<0.05) in BCL6B-transfected AGS cells than those in control vector transfected AGS cells. In BCL6B-transfected BGC823 cells, the proportions of both early apoptotic cells (15.99%±0.15% vs. 10.42%±0.63%, P<0.001) and late apoptotic cells (6.86%±0.42% vs. 4.53%±0.62%, P<0.01) were significantly increased compared with the control vector transfected cells.

In Vivo Tumor Suppression

BGC823/BCL6B or control cell line BGC823/vector was randomly injected into the dorsal flank of nude mice to compare the tumor growth patterns in vivo.

Figure 7:
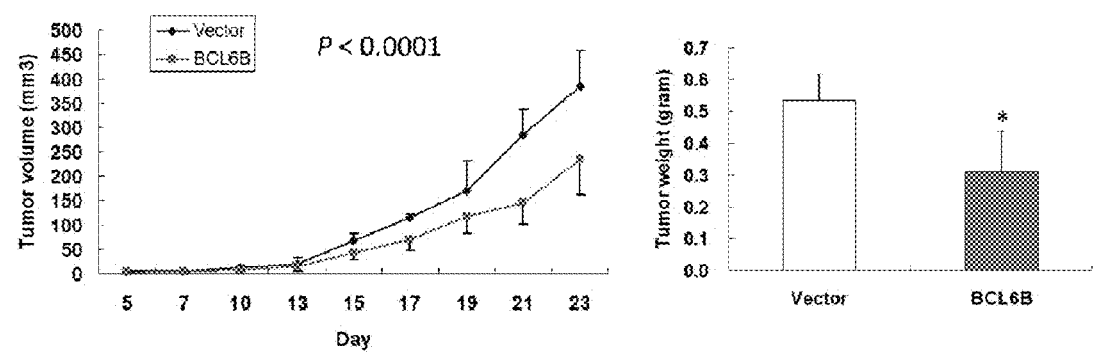
FIG. 7 shows the growth-inhibition effect of BCL6B expression in nude mice in an embodiment.

The tumor growth curve of BGC823 stably transfected with BCL6B or empty vector in vivo was shown in FIG. 7A. The tumor volume was significantly lower in BCL6B transfected nude mice as compared to the vector control mice (P<0.0001). At the end of experiments, tumors were isolated and weighted. The mean tumor weight was significantly lesser in BCL6B transfected nude mice as compared with the vector control mice (P<0.05) (FIG. 7B), indicating that BCL6B acts as a tumor suppressor in gastric carcinogenesis.

Methylation Status in GC Patients

The expression of BCL6B was significantly different in primary tumors and their adjacent non-tumor tissues, and showed correlation with methylation status in cancer cell lines.

Methylation Status in the GC Cell Lines by BGS

Figure 8:
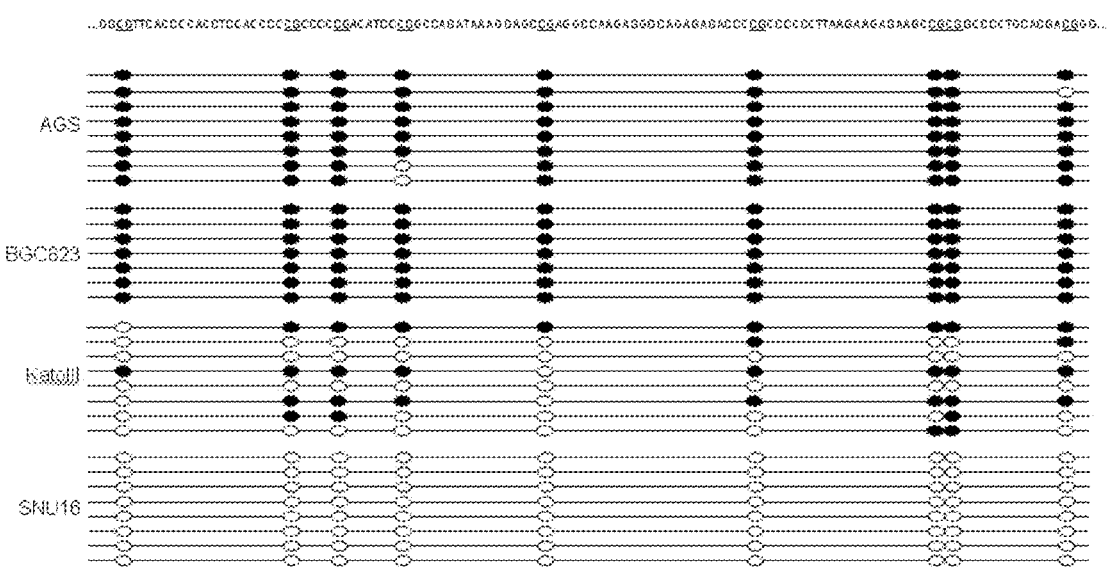
FIG. 8 shows the methylation status of BCL6B genomic sequence (SEQ ID NO:19) in GC cell lines by BGS in an embodiment.
Figure 9:
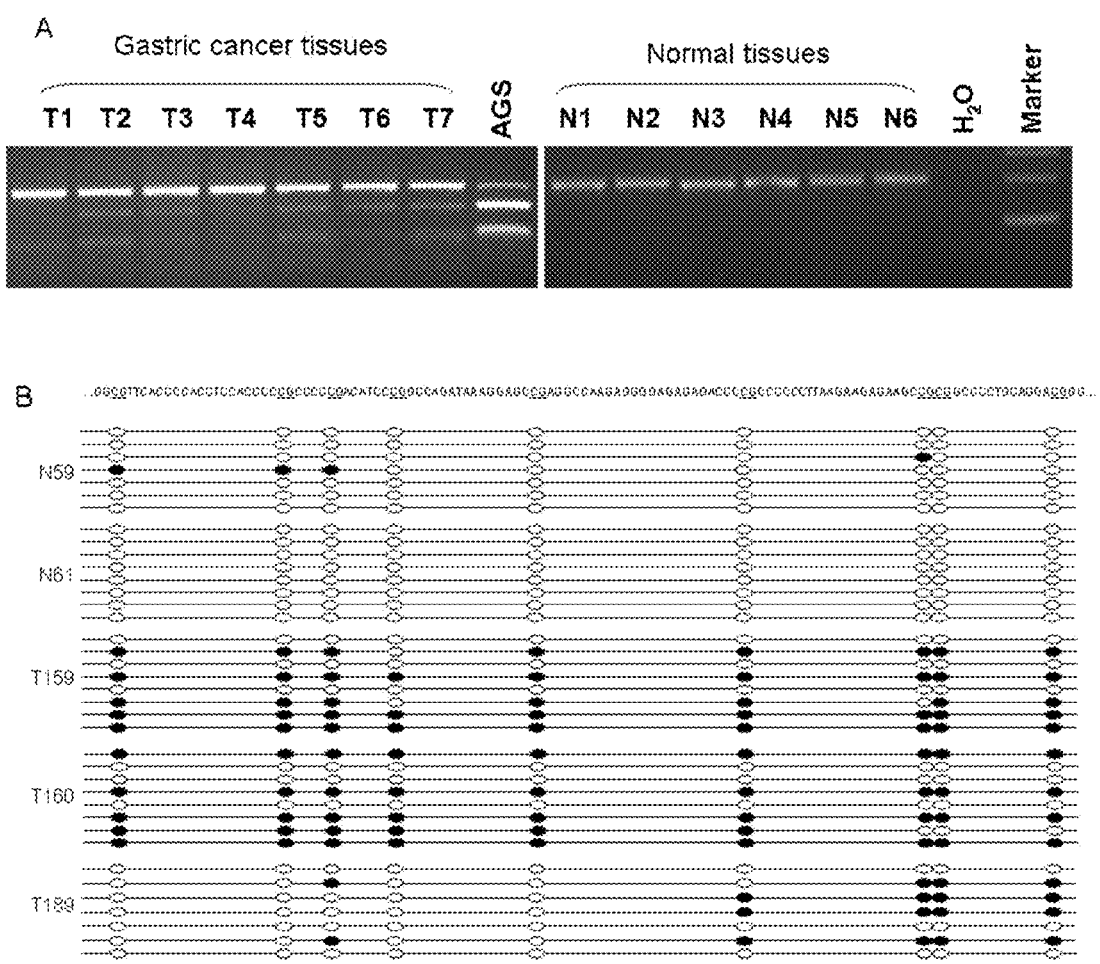
FIG. 9 shows the methylation status of BCL6B genomic sequence (SEQ ID NO:19) in primary GC and normal gastric tissue samples in an embodiment.

BGS was performed to evaluate methylation status on 4 GC cell line (AGS, BGC823, Kato III and SNU16). The BGS results were consistent with those of the MSP and COBRA (FIG. 8).

Methylation Status in the GC Tissues and Normal Gastric Tissues

BCL6B methylation status in 309 primary gastric cancers from two independent cohorts and twenty normal gastric biopsy specimens was investigated by COBRA. Aberrant methylation was detected in 169 tumor tissues (169 of 309; 55%), while 20 normal gastric biopsy specimens showed no methylation at all (FIG. 9A), indicating that BCL6B methylation is tumor-specific. Detailed BGS analyses of some samples also confirmed that the BCL6B promoter was frequently methylated in primary GC but not in normal gastric tissue (FIG. 9B)

Association Between BCL6B Methylation and Clinical Characteristics

To evaluate the clinical application of BCL6B in gastric tumors, the inventors analyzed the correlation between BCL6B methylation and clinical features including patient age, gender, tumor stage, *H. pylori* infection status, Lauren type, tumor differentiation, and survival data in two cohorts. There was no correlation between the methylation of BCL6B and clinicopathologic features such as age, *H. pylori* status, histologic type, or pathologic stage in cohort I, while methylation of BCL6B was found to be only associated with Lauren type in cohort II.

Figure 10:
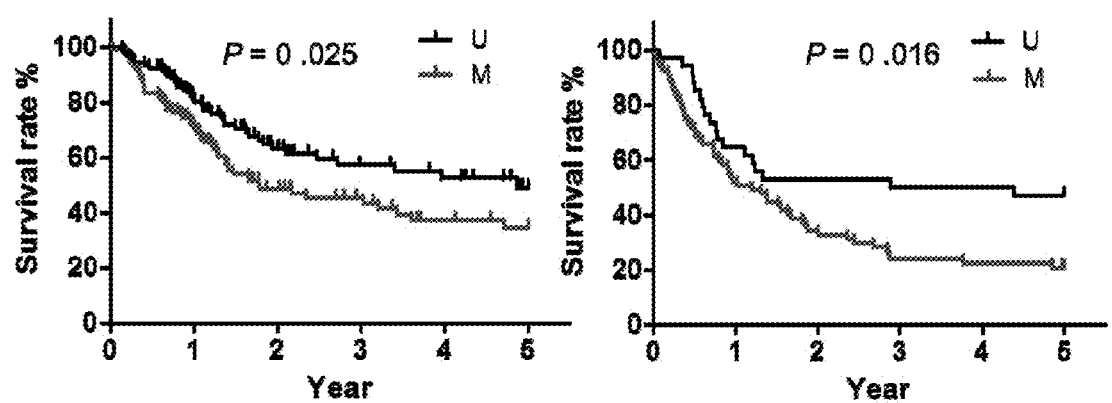
FIG. 10 shows a Kaplan-Meier analysis of gastric cancer patient survival in an embodiment.

In univariate Cox regression analysis of Cohort I, BCL6B methylation was associated with a significantly increased risk of cancer-related death (RR, 1.60; 95% confidence interval, 1.07-2.39; p=0.023). Tumor stage (P<0.0001) also was significant predictors of outcome. After the adjustment for potential confounding factors, multivariate Cox regression analysis showed that BCL6B methylation was a predictor of poorer survival of GC patients (RR, 2.14; 95% confidence interval, 1.36-3.36; P=0.001). Multivariate analysis revealed tumor TNM stage was another independent predictor for overall survival. Patients in stages I-III had a significantly better survival when compared with patients with a stage IV tumor. As shown in the Kaplan-Meier survival curves, gastric cancer patients with BCL6B methylated had significantly shorter survival than others (P=0.021, log-rank test) (FIG. 10A).

Cohort II was used to further validate the findings in cohort I. Similarly, univariate Cox regression analysis of Cohort II indicated that BCL6B methylation was associated with a significantly increased risk of cancer-related death (RR, 1.92; 95% confidence interval, 1.13-3.25; p=0.016). Tumor stage (P<0.006) also was significant predictors of outcome. In multivariate Cox regression analysis, BCL6B methylation was shown to have a marginal association with survival (P=0.055). As shown in the Kaplan-Meier survival curves, gastric cancer patients with BCL6B methylated had significantly shorter survival than others (P=0.012, log-rank test) (FIG. 10B).

All patents, patent applications, and other publications, including GenBank Accession Numbers, cited in this application are incorporated by reference in the entirety for all purposes.

TABLE 1

DNA sequences of primers used in this study

Primer name Sequence (5'-3')

A) RT-PCR primers for detecting BCL6B mRNA expression

| | | |
|---|---|---|
| BCL6BRTF | CTACGTCCGCGAGTTCACTC | SEQ ID NO: 1 |
| BCL6BRTR | CCCGGAAAATTGAATAGAAG | SEQ ID NO: 2 |

B) COBRA or BGS primers

| | | |
|---|---|---|
| BCL6BCOBRAF | GAGGAAGGAAGGATATAGATTTA | SEQ ID NO: 3 |
| BCL6BCOBRAR | CTTAAAAAACCCAAAAATCTAACT | SEQ ID NO: 4 |

| MSP Primer | Sequence (5'-3') | Sequence region amplified | |
|---|---|---|---|
| C) | | | |
| BCL6BmF1 | TTTTTATTTTCGTTTTCGATATTTC | -59 to +48 | SEQ ID NO: 5 |
| BCL6BmR1 | CCGTCCTACAAAAACCGCG | | SEQ ID NO: 6 |
| BCL6BuF1 | TTATTTTTATTTTTGTTTTTGATATTTT | | SEQ ID NO: 7 |
| BCL6BuR1 | CCCATCCTACAAAAACCACA | | SEQ ID NO: 8 |
| D) | | | |
| BCL6BmF2 | TTGTCGTATGTATTTTGTTTTGT | -370 to -191 | SEQ ID NO: 13 |
| BCL6BmR2 | ACTACAAATAAACACGAAAACG | | SEQ ID NO: 14 |
| BCL6BuF2 | TTGTTGTATGTATTTTGTTTTGT | | SEQ ID NO: 15 |
| BCL6BuR2 | CACTACAAATAAACACAAAAA | | SEQ ID NO: 16 |

```
INFORMAL SEQUENCE LISTING
                                                    SEQ ID NO: 1
primer BCL6BRTF
CTACGTCCGCGAGTTCACTC SEQ ID NO: 2
primer BCL6BRTR
CCCGGAAAATTGAATAGAAG SEQ ID NO: 3
primer BCL6BCOBRAF
GAGGAAGGAAGGATATAGATTTA SEQ ID NO: 4
primer BCL6BCOBRAR
CTTAAAAAACCCAAAAATCTAACT SEQ ID NO: 5
primer BCL6BmF1
TTTTTATTTTCGTTTTCGATATTTC SEQ ID NO: 6
primer BCL6BmR1
CCGTCCTACAAAAACCGCG SEQ ID NO: 7
primer BCL6BuF1
TTATTTTTATTTTTGTTTTTGATATTTT SEQ ID NO: 8
primer BCL6BuR1
CCCATCCTACAAAAACCACA SEQ ID NO: 9
the sequence of methylation specific PCR
product (-59 to +48 from the transcription
```

-continued start site)
CCTCCACCCCCGCCCCCGACATCCCGGCCAGATAAAGGAGCCGAGGCCAAGAGGGG

AGAGAGACCCCGCCCCCCTTAAGAAGAGAAGCCGCGGCCCCTGCAGGACGG

SEQ ID NO: 10
BCL6B protein coding cDNA sequence (1413 bp)
ATGGGTTCCCCGCCGCCCCGGAGGGAGCGCTGGGCTACGTCCGCGAGTTCACTCGC

CACTCCTCCGACGTGCTGGGCAACCTCAACGAGCTGCGCCTGCGCGGGATCCTCACT

GACGTCACGCTGCTGGTTGGCGGGCAACCCCTCAGAGCACACAAGGCAGTTCTCAT

CGCCTGCAGTGGCTTCTTCTATTCAATTTTCCGGGGCCGTGCGGGAGTCGGGGTGGA

CGTGCTCTCTCTGCCCGGGGGTCCCGAAGCGAGAGGCTTCGCCCCTCTATTGGACTT

CATGTACACTTCGCGCCTGCGCCTCTCTCCAGCCACTGCACCAGCAGTCCTAGCGGC

CGCCACCTATTTGCAGATGGAGCACGTGGTCCAGGCATGCCACCGCTTCATCCAGGC

CAGCTATGAACCTCTGGGCATCTCCCTGCGCCCCCTGGAAGCAGAACCCCCAACACC

CCCAACGGCCCCTCCACCAGGTAGTCCCAGGCGCTCCGAAGGACACCCAGACCCAC

CTACTGAATCTCGAAGCTGCAGTCAAGGCCCCCCCAGTCCAGCCAGCCCTGACCCCA

AGGCCTGCAACTGGAAAAAGTACAAGTACATCGTGCTAAACTCTCAGGCCTCCCAA

GCAGGGAGCCTGGTCGGGGAGAGAAGTTCTGGTCAACCTTGCCCCCAAGCCAGGCT

CCCCAGTGGAGACGAGGCCTCCAGCAGCAGCAGCAGCAGCAGCAGCAGTGAA

GAAAGGCTCTCTCCAACTGCTGCCACTGTGCAGTTCAAATGTGGGCTCCAGCCAGT

ACCCCCTACCTCCTCACATCCCAGGCTCAAGACACCTCTGGATCACCCTCTGAACGG

GCTCGTCCACTACCAGGAAGTGAATTTTTCAGCTGCCAGAACTGTGAGGCTGTGGCA

GGGTGCTCATCGGGGCTGGACTCCTTGGTTCCTGGGGACGAAGACAAACCCTATAA

GTGTCAGCTGTGCCGGTCTTCGTTCCGCTACAAGGGCAACCTTGCCAGTCATCGTAC

AGTGCACACAGGGGAAAAGCCTTACCACTGCTCAATCTGCGGAGCCCGTTTTAACC

GGCCAGCAAACCTGAAAACGCACAGCCGCATCCATTCGGGAGAGAAGCCGTATAAG

TGTGAGACGTGCGGCTCGCGCTTTGTACAGGTGGCACATCTGCGGGCGCACGTGCTG

ATCCACACCGGGGAGAAGCCCTACCCTTGCCCTACCTGCGGAACCCGCTTCCGCCAC

CTGCAGACCCTCAAGAGCCACGTTCGCATCCACACCGGAGAGAAGCCTTACCACTG

CGACCCCTGTGGCCTGCATTTCCGGCACAAGAGTCAACTGCGGCTGCATCTGCGCCA

GAAACACGGAGCTGCTACCAACACCAAAGTGCACTACCACATTCTCGGGGGGCCC

SEQ ID NO: 11
BCL6B full length cDNA sequence (GenBank
Accession No. NM_181844.3, 3544 bp)
GAGACCCCGCCCCCCTTAAGAAGAGAAGCCGCGGCCCCTGCAGGACGGGGGCCTGT

GTCGCTATGGGTTCCCCGCCGCCCCGGAGGGAGCGCTGGGCTACGTCCGCGAGTTC

ACTCGCCACTCCTCCGACGTGCTGGGCAACCTCAACGAGCTGCGCCTGCGCGGGATC

CTCACTGACGTCACGCTGCTGGTTGGCGGGCAACCCCTCAGAGCACACAAGGCAGT

TCTCATCGCCTGCAGTGGCTTCTTCTATTCAATTTTCCGGGGCCGTGCGGGAGTCGGG

GTGGACGTGCTCTCTCTGCCCGGGGGTCCCGAAGCGAGAGGCTTCGCCCCTCTATTG

GACTTCATGTACACTTCGCGCCTGCGCCTCTCTCCAGCCACTGCACCAGCAGTCCTA

GCGGCCGCCACCTATTTGCAGATGGAGCACGTGGTCCAGGCATGCCACCGCTTCATC

CAGGCCAGCTATGAACCTCTGGGCATCTCCCTGCGCCCCCTGGAAGCAGAACCCCCA

ACACCCCCAACGGCCCCTCCACCAGGTAGTCCCAGGCGCTCCGAAGGACACCCAGA

CCCACCTACTGAATCTCGAAGCTGCAGTCAAGGCCCCCCCAGTCCAGCCAGCCCTGA

-continued

```
CCCCAAGGCCTGCAACTGGAAAAAGTACAAGTACATCGTGCTAAACTCTCAGGCCT

CCCAAGCAGGGAGCCTGGTCGGGGAGAGAAGTTCTGGTCAACCTTGCCCCCAAGCC

AGGCTCCCCAGTGGAGACGAGGCCTCCAGCAGCAGCAGCAGCAGCAGCAGCA

GCAGTGAAGAAGGACCCATTCCTGGTCCCCAGAGCAGGCTCTCTCCAACTGCTGCCA

CTGTGCAGTTCAAATGTGGGGCTCCAGCCAGTACCCCCTACCTCCTCACATCCCAGG

CTCAAGACACCTCTGGATCACCCTCTGAACGGGCTCGTCCACTACCGGGAAGTGAAT

TTTTCAGCTGCCAGAACTGTGAGGCTGTGGCAGGGTGCTCATCGGGGCTGGACTCCT

TGGTTCCTGGGGACGAAGACAAACCCTATAAGTGTCAGCTGTGCCGGTCTTCGTTCC

GCTACAAGGGCAACCTTGCCAGTCACCGTACAGTGCACACAGGGGAAAAGCCTTAC

CACTGCTCAATCTGCGGAGCCCGTTTTAACCGGCCAGCAAACCTGAAAACGCACAG

CCGCATCCATTCGGGAGAGAAGCCGTATAAGTGTGAGACGTGCGGCTCGCGCTTTGT

ACAGGTGGCACATCTGCGGGCGCACGTGCTGATCCACACCGGGGAGAAGCCCTACC

CTTGCCCTACCTGCGGAACCCGCTTCCGCCACCTGCAGACCCTCAAGAGCCACGTTC

GCATCCACACCGGAGAGAAGCCTTACCACTGCGACCCCTGTGGCCTGCATTTCCGGC

ACAAGAGTCAACTGCGGCTGCATCTGCGCCAGAAACACGGAGCTGCTACCAACACC

AAAGTGCACTACCACATTCTCGGGGGGCCCTAGCTGAGCGCAGGCCCAGGCCCCAC

TTGCTTCCTGCGGGTGGGAAAGCTGCAGGCCCAGGCCTTGCTTCCCTATCAGGCTTG

GGCATAGGGGTGTGCCAGGCCACTTTGGTATCAGAAATTGCCACCCTCTTAATTTCT

CACTGGGGAGAGCAGGGGTGGCAGATCCTGGCTAGATCTGCCTCTGTTTTGCTGGTC

AAAACCTCTTCCCCACAAGCCAGATTGTTTCTGAGGAGAGAGCTAGCTAGGGGCTG

GGAAAGGGGAGAGATTGGAGTCCTGGTCTCCCTAAGGGAATAGCCCTCCACCTGTG

GCCCCCATTGCATTCAGTTTATCTGTAAATATAATTTATTGAGGCCTTTGGGTGGCAC

CGGGGCCTTCATTCGATTGCATTTCCCACTCCCCTCTTCCACAAGTGTGATTAAAAGT

GACCAGAAACACAGAAGGTGAGATCACAGCTCTGCTGGCAGAGATTACTAGCCCTT

GGCTCTCTCGTTTGGCTTGGGTATTTTATATTATTTCTGTCATAACTTTTATCTTTAGA

ATTGTTCTTTCTCCTGTTTGTTTGCTTGTTAGTTTGTTTAAAATGGAAAAAGGGGTTC

TCTGTGTTCTGCCCCTGTAATTCTAGGTCTGGAACCTTTATTTGTTCTAGGGCAGCTC

TGGGAACATGCGGGATTGTGGAATTGGGTCAGGAACCCTCTCTGGTATTCTGGATGT

TGTAGGTTCTCTAGCAGTCTAGAAATGGATACAGACATTTCTCTGTTCTTCAAGGGT

GATAGGAACCATTATGTTGAGCCCAAAATGGAAGTAATAAATGCCTCCTGGAG

GCTGTGGGTGTGGGGATTCTGTATCTGGATTCCGTATCACTCCAAGTGGAGGCTGG

CAGGTTTTTCTGCAAGATGGTCCAGAATCTAAAATGTCCCATTAATCTGGTCACTTG

GGTTTGGCTCTGCTGTATCCATCTATAGTGGTAGAGACCCACCAGGGCTCAAGTGGA

GTCCATCATCCTCCCACGGGGCCTGTTCTTAGCACTGAGTTGATCGCTCCATGGGG

GAGAGATCAGACATTCCTTATCAGAGATGATGTGACCTTTTCTGACTCTGCCCAGTC

TCTATGAATGTTATGGCCTAGGGAAGAATCATGAAACTCTTTAGCTTGATTAGATGG

TAAACAGTGTTAACCCATCCTTTACTACAGAGGCATATGGGTTTGAATGTTACCTGG

GGTTCTCTCTATTGAGTTGAGCCCCTTCTTCCTTTAGTGGGTTTTGGACATCTTCTGG

CAAGTGTCCAGATGCCAGAACCTTCTTTTCCTCTAGAAGGGATGGTGCTTGGTAACC

TTACCTTTTAAAAGCTGGGTCTGTGACCTGGTCTTCCCATCCCTGCATTCCTGTCTGG
```

```
                                                       -continued
AACCAGTGAATGCATTAGAACCTTCCATAGGAAAAGAAAAGGGGCTGAGTTCCATT

CTGGGTTTGCTGTAGTTTGGTTGGGATTATTGTTGGCATTACAGATGTAAAAGATTG

ACTAGCCCATAGGCCAAAGGCCTGTTCTAGTTGACCAAGTTTCAAGTAGGATTAAGA

GGTTGGTTGAGGGGTGCAGTTTCTGGTGTAGGCCAGGTAGGTAGAAAGTGAGGAAC

AGGGTTGCCTCTTGGCTGGGTGGAGTCTCTGAAATGTTAGAAGAAGCGCTGAAGCCT

TGATTGATAGTTCTGCCCCTTGTTGCCCTGGGGCTTATCTGATTATGGGACGAGGGT

AGAAAGTAAGAAGCACTTTTGAATTTGTGGGGTAGAACTTCAACAATAAGTCAGTTC

TAGTGGCTGTCGCCTGGGGACTAGTGAGAAAGCTACTCTTCTCCCTCTTCCCTCTTTC

TCCCCATGGCCCCACTGCAGAATTAAAGAAGGAAGAAGGGAAGGCGGAGGAGTCTA

TAAGAAGGAATCATGATTTCTATTTAGCAGATTGGATGGGCAGGTGGAGAATGCCT

GGGGGTAGAAATGTTAGATCTTGCAACATCAGATCCTTGGAATAAAGAAGCCTCTCT

GTGCAAAAAAAAAAAAAAA
                                                       SEQ ID NO: 12
Partial coding sequence used to detect human
BCL6B mRNA (170 bp)
CTACGTCCGCGAGTTCACTCGCCACTCCTCCGACGTGCTGGGCAACCTCAACGAGCT

GCGCCTGCGCGGGATCCTCACTGACGTCACGCTGCTGGTTGGCGGGCAACCCCTCAG

AGCACACAAGGCAGTTCTCATCGCCTGCAGTGGCTTCTTCTATTCAATTTTCCGGG
                                                       SEQ ID NO: 13
primer BCL6BmF2
TTGTCGTATGTATTTTGTTTTGT
                                                       SEQ ID NO: 14
primer BCL6BmR2
ACTACAAATAAACACGAAAACG
                                                       SEQ ID NO: 15
primer BCL6BuF2
TTGTTGTATGTATTTTGTTTTGT
                                                       SEQ ID NO: 16
primer BCL6BuR2
CACTACAAATAAACACAAAAA
                                                       SEQ ID NO: 17
BCL6B_HUMAN B-cell CLL/lymphoma 6, member B, 480 amino acids
MGSPAAPEGALGYVREFTRHSSDVLGNLNELRLRGILTDVTLLVGGQPLRAHKAVLIAC

SGFFYSIFRGRAGVGVDVLSLPGGPEARGFAPLLDFMYTSRLRLSPATAPAVLAAATYL

QMEHVVQACHRFIQASYEPLGISLRPLEAEPPTPPTAPPPGSPRRSEGHPDPPTESRSCSQG

PPSPASPDPKACNWKKYKYIVLNSQASQAGSLVGERSSGQPCPQARLPSGDEASSSSSSS

SSSSSEEGPIPGPQSRLSPTAATVQFKCGAPASTPYLLTSQAQDTSGSPSERARPLPGSEFF

SCQNCEAVAGCSSGLDSLVPGDEDKPYKCQLCRSSFRYKGNLASHRTVHTGEKPYHCSI

CGARFNRPANLKTHSRIHSGEKPYKCETCGSRFVQVAHLRAHVLIHTGEKPYPCPTCGT

RFRHLQTLKSHVRIHTGEKPYHCDPCGLHFRHKSQLRLHLRQKHGAATNTKVHYHILG

GP
                                                       SEQ ID NO: 18
Sequence of promoter region of BCL6B gene for
combined bisulfite restriction analysis (-95 to
+95 bp relative to the transcription start site)
GAGGAAGGAAGGATACAGACCCAGGCGTTCACCCCACCTCCACCCCCGCCCCCGAC

ATCCCGGCCAGATAAAGGAGCCGAGGCCAAGAGGGGAGAGAGACCCCGCCCCCCTT

AAGAAGAGAAGCCGCGCCCCTGCAGGACGGGGGTAAGAACAAGAGACTGAGGGA

GCCAGACTCCTGGGTCCCCCAAG
```

SEQ ID NO: 19
Sequence of promoter region of BCL6B gene for
bisulfite genomic sequencing (-72 to +49 from
the transcription start site)
GGCGTTCACCCCACCTCCACCCCGCCCCGACATCCCGGCCAGATAAAGGAGCCG

AGGCCAAGAGGGGAGAGAGACCCCGCCCCCCTTAAGAAGAGAAGCCGCGGCCCCT

GCAGGACGGG

SEQ ID NO: 20
Sequence of CpG island of BCL6B gene (-869 to
+33 from the transcription start site)
CCTTGCCTACTTGCCGCGCTGGACCCCGGCGTCCCGCCAGCCTCCAAGCGTAGCCGA

CGGGCGGGTGCCCGAGGCCCTCGTGAGCTGGGATTGGGGGAAAGCAAGCGGGCTTT

GGGCGGGAGTCCATCTCTCTGGATCCCTACAAGGACCCAGAAGAGAGTCGGGAGCG

AGAGAGGCCGGACGCCTAGGTCTCCCGAGCGTCTCTCGCCCCTCCACCCCCACCTCG

GGGCTTTCCCCACCTCCTCGAGGGGAAGCAGCTGGCGGAGCCGTCCGGTCGCAGGA

CAATGGAAGGAAACCAACTAGAAATCATATCCGCCCTCTCCGTACCCCGCCCGGCC

AGAGCCCCCTTTTTGTAGGCCCGGGTAGAGTAGCCTGTCATTCACACCACACCCTC

CCCGTCTGAGACCCTACGGGAGCCCACTGTCGTCTGCCCAAACCTGCTGTCTCGTTG

GGCTCCCCCTTTTCTCCCTTAACACAGTACAAGAGAGGGAGAGGGGTTGCCGTATG

CACTTTGTCCTGCAGCAAAGGTTGGCTCCTGGCAAACCCTCCCAAAAGCCAACACAC

CAATTTTCACTGGCCCAGGCCTTCCGACGACTCAGACTCCCGTATTGCCAACCTCGA

TATCCCTAACCTCCTCCCCAATTCCAATATCCCCGTCCTCGTGTCCACTTGCAGTGAC

CCAAGACCCCCTACGTTACGACCACCCCTTGTTTCTGAGGTCCCGCCCTCGAGACGG

AGACCCCGCCCTGGACTCGCCATCTGGAGAGCGAGGGAGGAAGGAAGGATACAGA

CCCAGGCGTTCACCCCACCTCCACCCCGCCCCGACATCCCGGCCAGATAAAGGA

GCCGAGGCCAAGAGGGGAGAGAGACCCCGCCCCCCTTAAGAAGAGAAGCCGCG

---

What is claimed is:

1. A method for detecting risk of gastric cancer in a subject in need thereof, comprising the steps of:
   (a) treating a gastric mucosal sample taken from the subject with an enzyme that preferentially cleaves methylated DNA or a bisulfate that differentially modifies methylated and unmethylated DNA; and
   (b) determining whether each cytosine-guanine dinucleotide (CpG) in a CpG-containing genomic sequence is methylated or unmethylated, wherein the CpG-containing genomic sequence is selected from the group consisting of SEQ ID NO:9, 18, 19, or 20 and comprising at least one CpG, wherein the presence of one methylated CpG in the CpG-containing genomic sequence indicates the subject is at risk for gastric cancer.

2. The method of claim 1, wherein CpG-containing genomic sequence is SEQ ID NO:19, and wherein at least 5 of all CpG being methylated indicates the subject is at risk for gastric cancer.

3. The method of claim 1, when the subject is indicated at risk for gastric cancer, further comprising repeating steps (a) and (b) at a later time using the sample type of sample from the subject, wherein an increase in the number of methylated CpG at the later time as compared to the number of methylated CpG determined from the original step (b) indicates an elevated risk of gastric cancer, and a decrease indicates a decreased risk of gastric cancer.

4. The method of claim 1, wherein step (b) comprises an amplification reaction.

* * * * *

SEQUENCE LISTING

<160> NUMBER OF SEQ ID NOS: 20

<210> SEQ ID NO 1
<211> LENGTH: 20
<212> TYPE: DNA
<213> ORGANISM: Artificial Sequence
<220> FEATURE:
<223> OTHER INFORMATION: synthetic RT-PCR primer BCL6BRTF for detecting
      BCL6B mRNA expression

<400> SEQUENCE: 1
ctacgtccgc gagttcactc                                               20

<210> SEQ ID NO 2
<211> LENGTH: 20
<212> TYPE: DNA
<213> ORGANISM: Artificial Sequence
<220> FEATURE:
<223> OTHER INFORMATION: synthetic RT-PCR primer BCL6BRTR for detecting
      BCL6B mRNA expression

<400> SEQUENCE: 2
cccggaaaat tgaatagaag                                               20

<210> SEQ ID NO 3

```
<211> LENGTH: 23
<212> TYPE: DNA
<213> ORGANISM: Artificial Sequence
<220> FEATURE:
<223> OTHER INFORMATION: synthetic combined bisulfite restriction
      analysis (COBRA) or bisulfite genomic sequencing (BGS) primer
      BCL6BCOBRAF

<400> SEQUENCE: 3
gaggaaggaa ggatatagat tta                                            23

<210> SEQ ID NO 4
<211> LENGTH: 24
<212> TYPE: DNA
<213> ORGANISM: Artificial Sequence
<220> FEATURE:
<223> OTHER INFORMATION: synthetic combined bisulfite restriction
      analysis (COBRA) or bisulfite genomic sequencing (BGS) primer
      BCL6BCOBRAR

<400> SEQUENCE: 4
cttaaaaaac ccaaaaatct aact                                           24

<210> SEQ ID NO 5
<211> LENGTH: 25
<212> TYPE: DNA
<213> ORGANISM: Artificial Sequence
<220> FEATURE:
<223> OTHER INFORMATION: synthetic methylation specific PCR (MSP) primer
      BCL6BmF1

<400> SEQUENCE: 5
tttttatttt cgttttcgat atttc                                          25

<210> SEQ ID NO 6
<211> LENGTH: 19
<212> TYPE: DNA
<213> ORGANISM: Artificial Sequence
<220> FEATURE:
<223> OTHER INFORMATION: synthetic methylation specific PCR (MSP) primer
      BCL6BmR1

<400> SEQUENCE: 6
ccgtcctaca aaaccgcg                                                  19

<210> SEQ ID NO 7
<211> LENGTH: 28
<212> TYPE: DNA
<213> ORGANISM: Artificial Sequence
<220> FEATURE:
<223> OTHER INFORMATION: synthetic methylation specific PCR (MSP) primer
      BCL6BuF1

<400> SEQUENCE: 7
ttatttttat ttttgttttt gatatttt                                       28

<210> SEQ ID NO 8
<211> LENGTH: 20
<212> TYPE: DNA
<213> ORGANISM: Artificial Sequence
<220> FEATURE:
<223> OTHER INFORMATION: synthetic methylation specific PCR (MSP) primer
      BCL6BuR1

<400> SEQUENCE: 8
cccatcctac aaaaccaca                                                 20

<210> SEQ ID NO 9
```

```
<211> LENGTH: 107
<212> TYPE: DNA
<213> ORGANISM: Homo sapiens
<220> FEATURE:
<223> OTHER INFORMATION: syntheticmethylation specific PCR (MSP)
      product, MSP amplicon region -59 - +48 relative to transcription
      start site

<400> SEQUENCE: 9
cctccacccc cgcccccgac atcccggcca gataaaggag ccgaggccaa gaggggagag    60 agacccccgcc cccccttaaga agagaagccg cggcccctgc aggacgg                107

<210> SEQ ID NO 10
<211> LENGTH: 1413
<212> TYPE: DNA
<213> ORGANISM: Homo sapiens
<220> FEATURE:
<223> OTHER INFORMATION: B-cell CLL/lymphoma 6, member B (BCL6B),
      bcl6-associated zinc finger protein, zinc finger protein 62
      (ZNF62), ZBTB28, BAZF protein coding sequence, partial cDNA

<400> SEQUENCE: 10
atgggttccc ccgccgcccc ggagggagcg ctgggctacg tccgcgagtt cactcgccac    60
tcctccgacg tgctgggcaa cctcaacgag ctgcgcctgc gcgggatcct cactgacgtc   120
acgctgctgg ttggcgggca accccctcaga gcacacaagg cagttctcat cgcctgcagt   180
ggcttcttct attcaatttt ccggggccgt gcgggagtcg ggtggacgt gctctctctg    240 cccgggggtc ccgaagcgag aggcttcgcc cctctattgg acttcatgta cacttcgcgc   300
ctgcgcctct ctccagccac tgcaccagca gtcctagcgg ccgccaccta tttgcagatg   360
gagcacgtgg tccaggcatg ccaccgcttc atccaggcca gctatgaacc tctgggcatc   420
tccctgcgcc cctggaagc agaaccccca acacccccaa cggcccctcc accaggtagt   480
cccaggcgct ccgaaggaca cccagaccca cctactgaat ctcgaagctg cagtcaaggc   540 cccccccagtc cagccagccc tgaccccaag gcctgcaact ggaaaaagta caagtacatc   600 gtgctaaaact ctcaggcctc ccaagcaggg agcctggtcg gggagagaag ttctggtcaa   660
ccttgccccc aagccaggct ccccagtgga gacgaggcct ccagcagcag cagcagcagc   720
agcagcagca gtgaagaaag gctctctcca actgctgcca ctgtgcagtt caaatgtggg   780
gctccagcca gtacccccta cctcctcaca tcccaggctc aagacacctc tggatcaccc   840
tctgaacggg ctcgtccact accaggaagt gaatttttca gctgccagaa ctgtgaggct   900
gtggcagggt gctcatcggg gctggactcc ttggttcctg gggacgaaga caaaccctat   960
aagtgtcagc tgtgccggtc ttcgttccgc tacaagggca accttgccag tcatcgtaca  1020
gtgcacacag gggaaaagcc ttaccactgc tcaatctgcg gagcccgttt taaccggcca  1080
gcaaacctga aaacgcacag ccgcatccat tcgggagaga agccgtataa gtgtgagacg  1140
tgcggctcgc gctttgtaca ggtggcacat ctgcgggcgc acgtgctgat ccacaccggg  1200
gagaagccct acccttgccc tacctgcgga acccgcttcc gccacctgca gaccctcaag  1260
agccacgttc gcatccacac cggagagaag ccttaccact gcgaccccctg tggcctgcat  1320 ttccggcaca agagtcaact gcggctgcat ctgcgccaga acacggagc tgctaccaac  1380 accaaagtgc actaccacat tctcgggggg ccc                               1413

<210> SEQ ID NO 11
<211> LENGTH: 3544
<212> TYPE: DNA
<213> ORGANISM: Homo sapiens
<220> FEATURE:
```

<223> OTHER INFORMATION: B-cell CLL/lymphoma 6, member B (BCL6B), bcl6-associated zinc finger protein, zinc finger protein 62 (ZNF62), ZBTB28, BAZF full length cDNA

<400> SEQUENCE: 11

| | | | | | |
|---|---|---|---|---|---|
| gagaccccgc | cccccttaag | aagagaagcc | gcggcccctg | caggacgggg | gcctgtgtcg | 60 |
| ctatgggttc | ccccgccgcc | ccggagggag | cgctgggcta | cgtccgcgag | ttcactcgcc | 120 |
| actcctccga | cgtgctgggc | aacctcaacg | agctgcgcct | cgcgggatc | ctcactgacg | 180 |
| tcacgctgct | ggttggcggg | caaccectca | gagcacacaa | ggcagttctc | atcgcctgca | 240 |
| gtggcttctt | ctattcaatt | ttccggggcc | gtgcgggagt | cggggtggac | gtgctctctc | 300 |
| tgcccggggg | tcccgaagcg | agaggcttcg | cccctctatt | ggacttcatg | tacacttcgc | 360 |
| gcctgcgcct | ctctccagcc | actgcaccag | cagtcctagc | ggccgccacc | tatttgcaga | 420 |
| tggagcacgt | ggtccaggca | tgccaccgct | tcatccaggc | cagctatgaa | cctctgggca | 480 |
| tctccctgcg | cccccctggaa | gcagaacccc | caacaccccc | aacggcccct | ccaccaggta | 540 |
| gtcccaggcg | ctccgaagga | cacccagacc | cacctactga | atctcgaagc | tgcagtcaag | 600 |
| gccccccag | tccagccagc | cctgacccca | aggcctgcaa | ctggaaaaag | tacaagtaca | 660 |
| tcgtgctaaa | ctctcaggcc | tcccaagcag | ggagcctggt | cggggagaga | agttctggtc | 720 |
| aaccttgccc | ccaagccagg | ctccccagtg | gagacgaggc | ctccagcagc | agcagcagca | 780 |
| gcagcagcag | cagcagtgaa | gaaggaccca | ttcctggtcc | ccagagcagg | ctctctccaa | 840 |
| ctgctgccac | tgtgcagttc | aaatgtgggg | ctccagccag | tacccctac | ctcctcacat | 900 |
| cccaggctca | agacacctct | ggatcaccct | ctgaacgggc | tcgtccacta | ccgggaagtg | 960 |
| aattttcag | ctgccagaac | tgtgaggctg | tggcagggtg | ctcatcgggg | ctggactcct | 1020 |
| tggttcctgg | ggacgaagac | aaaccctata | agtgtcagct | gtgccggtct | tcgttccgct | 1080 |
| acaagggcaa | ccttgccagt | caccgtacag | tgcacacagg | ggaaaagcct | taccactgct | 1140 |
| caatctgcgg | agcccgtttt | aaccggccag | caaacctgaa | aacgcacagc | cgcatccatt | 1200 |
| cgggagagaa | gccgtataag | tgtgagacgt | gcggctcgcg | ctttgtacag | gtggcacatc | 1260 |
| tgcgggcgca | cgtgctgatc | cacaccgggg | agaagcccta | cccttgccct | acctgcggaa | 1320 |
| cccgcttccg | ccacctgcag | accctcaaga | gccacgttcg | catccacacc | ggagagaagc | 1380 |
| cttaccactg | cgacccctgt | ggcctgcatt | tccggcacaa | gagtcaactg | cggctgcatc | 1440 |
| tgcgccagaa | acacggagct | gctaccaaca | ccaaagtgca | ctaccacatt | ctcgggggc | 1500 |
| cctagctgag | cgcaggccca | ggccccactt | gcttcctgcg | ggtgggaaag | ctgcaggccc | 1560 |
| aggccttgct | tccctatcag | gcttgggcat | aggggtgtgc | caggccactt | tggtatcaga | 1620 |
| aattgccacc | ctcttaattt | ctcactgggg | agagcagggg | tggcagatcc | tggctagatc | 1680 |
| tgcctctgtt | ttgctggtca | aaacctcttc | cccacaagcc | agattgtttc | tgaggagaga | 1740 |
| gctagctagg | ggctgggaaa | ggggagagat | tggagtcctg | gtctccctaa | gggaatagcc | 1800 |
| ctccacctgt | ggcccccatt | gcattcagtt | tatctgtaaa | tataatttat | tgaggccttt | 1860 |
| gggtggcacc | ggggccttca | ttcgattgca | tttcccactc | ccctcttcca | caagtgtgat | 1920 |
| taaaagtgac | cagaaacaca | gaaggtgaga | tcacagctct | gctggcagag | attactagcc | 1980 |
| cttggctctc | tcgtttggct | tgggtatttt | atattatttc | tgtcataact | tttatcttta | 2040 |
| gaattgttct | ttctcctgtt | tgtttgcttg | ttagtttgtt | taaaatggaa | aaggggttc | 2100 |
| tctgtgttct | gccctgtaa | ttctaggtct | ggaacccttta | tttgttctag | ggcagctctg | 2160 |
| ggaacatgcg | ggattgtgga | attgggtcag | gaaccctctc | tggtattctg | gatgttgtag | 2220 |

```
gttctctagc agtctagaaa tggatacaga catttctctg ttcttcaagg gtgataggaa    2280
ccattatgtt gagcccaaaa tggaagtaat aataaatgcc tcctggaggc tgtgggtgtg    2340
ggggattctg tatctggatt ccgtatcact ccaagtggag gctggcaggt ttttctgcaa    2400
gatggtccag aatctaaaat gtcccattaa tctggtcact tgggtttggc tctgctgtat    2460
ccatctatag tggtagagac ccaccagggc tcaagtggag tccatcatcc tcccacgggg    2520
gcctgttctt agcactgagt tgatcgctcc atggggagga gatcagacat tccttatcag    2580
agatgatgtg accttttctg actctgccca gtctctatga atgttatggc ctagggaaga    2640
atcatgaaac tctttagctt gattagatgg taaacagtgt taacccatcc tttactacag    2700
aggcatatgg gtttgaatgt tacctgggt tctctctatt gagttgagcc ccttcttcct    2760
ttagtgggtt ttggacatct tctggcaagt gtccagatgc cagaaccttc ttttcctcta    2820
gaagggatgg tgcttggtaa ccttaccttt taaaagctgg gtctgtgacc tggtcttccc    2880
atccctgcat tcctgtctgg aaccagtgaa tgcattagaa ccttccatag gaaaagaaaa    2940
ggggctgagt tccattctgg gtttgctgta gtttggttgg gattattgtt ggcattacag    3000
atgtaaaaga ttgactagcc cataggccaa aggcctgttc tagttgacca gtttcaagt     3060 aggattaaga ggttggttga ggggtgcagt ttctggtgta ggccaggtag gtagaaagtg    3120
aggaacaggg ttgcctcttg gctggtgga gtctctgaaa tgttagaaga agcgctgaag    3180
ccttgattga tagttctgcc ccttgttgcc ctggggctta tctgattatg ggacgagggt    3240
agaaagtaag aagcactttt gaatttgtgg ggtagaactt caacaataag tcagttctag    3300
tggctgtcgc ctggggacta gtgagaaagc tactcttctc cctcttccct ctttctcccc    3360
atggccccac tgcagaatta agaaggaag aagggaaggc ggaggagtct ataagaagga    3420
atcatgattt ctatttagca gattggatgg gcaggtggag aatgcctggg ggtagaaatg    3480
ttagatcttg caacatcaga tccttggaat aaagaagcct ctctgtgcaa aaaaaaaaa    3540 aaaa                                                                 3544

<210> SEQ ID NO 12
<211> LENGTH: 170
<212> TYPE: DNA
<213> ORGANISM: Artificial Sequence
<220> FEATURE:
<223> OTHER INFORMATION: synthetic B-cell CLL/lymphoma 6, member B
      (BCL6B), bcl6-associated zinc finger protein, zinc finger protein
      62 (ZNF62), ZBTB28, BAZF partial coding sequence used to detect
      BCL6B mRNA, polynucleotide probe

<400> SEQUENCE: 12
ctacgtccgc gagttcactc gccactcctc cgacgtgctg ggcaacctca acgagctgcg    60
cctgcgcggg atcctcactg acgtcacgct gctggttggc gggcaacccc tcagagcaca   120
caaggcagtt ctcatcgcct gcagtggctt cttctattca attttccggg                170

<210> SEQ ID NO 13
<211> LENGTH: 23
<212> TYPE: DNA
<213> ORGANISM: Artificial Sequence
<220> FEATURE:
<223> OTHER INFORMATION: synthetic methylation specific PCR (MSP) primer
      BCL6BmF2

<400> SEQUENCE: 13
ttgtcgtatg tattttgttt tgt                                             23

<210> SEQ ID NO 14
```

```
<211> LENGTH: 22
<212> TYPE: DNA
<213> ORGANISM: Artificial Sequence
<220> FEATURE:
<223> OTHER INFORMATION: synthetic methylation specific PCR (MSP) primer
      BCL6BmR2

<400> SEQUENCE: 14
actacaaata aacacgaaaa cg                                            22

<210> SEQ ID NO 15
<211> LENGTH: 23
<212> TYPE: DNA
<213> ORGANISM: Artificial Sequence
<220> FEATURE:
<223> OTHER INFORMATION: synthetic methylation specific PCR (MSP) primer
      BCL6BuF2

<400> SEQUENCE: 15
ttgttgtatg tattttgttt tgt                                           23

<210> SEQ ID NO 16
<211> LENGTH: 21
<212> TYPE: DNA
<213> ORGANISM: Artificial Sequence
<220> FEATURE:
<223> OTHER INFORMATION: synthetic methylation specific PCR (MSP) primer
      BCL6BuR2

<400> SEQUENCE: 16
cactacaaat aaacacaaaa a                                             21

<210> SEQ ID NO 17
<211> LENGTH: 480
<212> TYPE: PRT
<213> ORGANISM: Homo sapiens
<220> FEATURE:
<223> OTHER INFORMATION: human B-cell CLL/lymphoma 6, member B (BCL6B),
      bcl6-associated zinc finger protein, zinc finger protein 62
      (ZNF62), ZBTB28, BAZF

<400> SEQUENCE: 17
```

Met Gly Ser Pro Ala Ala Pro Glu Gly Ala Leu Gly Tyr Val Arg Glu
1               5                   10                  15

Phe Thr Arg His Ser Ser Asp Val Leu Gly Asn Leu Asn Glu Leu Arg
            20                  25                  30

Leu Arg Gly Ile Leu Thr Asp Val Thr Leu Leu Val Gly Gly Gln Pro
        35                  40                  45

Leu Arg Ala His Lys Ala Val Leu Ile Ala Cys Ser Gly Phe Phe Tyr
    50                  55                  60

Ser Ile Phe Arg Gly Arg Ala Gly Val Gly Val Asp Val Leu Ser Leu
65                  70                  75                  80

Pro Gly Gly Pro Glu Ala Arg Gly Phe Ala Pro Leu Leu Asp Phe Met
                85                  90                  95

Tyr Thr Ser Arg Leu Arg Leu Ser Pro Ala Thr Ala Pro Ala Val Leu
            100                 105                 110

Ala Ala Ala Thr Tyr Leu Gln Met Glu His Val Val Gln Ala Cys His
        115                 120                 125

Arg Phe Ile Gln Ala Ser Tyr Glu Pro Leu Gly Ile Ser Leu Arg Pro
    130                 135                 140

Leu Glu Ala Glu Pro Pro Thr Pro Pro Thr Ala Pro Pro Gly Ser
145                 150                 155                 160

Pro Arg Arg Ser Glu Gly His Pro Asp Pro Pro Thr Glu Ser Arg Ser

```
                     165                 170                 175
Cys Ser Gln Gly Pro Ser Pro Ala Ser Pro Asp Pro Lys Ala Cys
            180                 185                 190

Asn Trp Lys Lys Tyr Lys Tyr Ile Val Leu Asn Ser Gln Ala Ser Gln
        195                 200                 205

Ala Gly Ser Leu Val Gly Glu Arg Ser Gly Gln Pro Cys Pro Gln
        210                 215                 220

Ala Arg Leu Pro Ser Gly Asp Glu Ala Ser Ser Ser Ser Ser Ser
225                 230                 235                 240

Ser Ser Ser Ser Glu Glu Gly Pro Ile Pro Gly Pro Gln Ser Arg
            245                 250                 255

Leu Ser Pro Thr Ala Ala Thr Val Gln Phe Lys Cys Gly Ala Pro Ala
            260                 265                 270

Ser Thr Pro Tyr Leu Leu Thr Ser Gln Ala Gln Asp Thr Ser Gly Ser
        275                 280                 285

Pro Ser Glu Arg Ala Arg Pro Leu Pro Gly Ser Glu Phe Phe Ser Cys
        290                 295                 300

Gln Asn Cys Glu Ala Val Ala Gly Cys Ser Ser Gly Leu Asp Ser Leu
305                 310                 315                 320

Val Pro Gly Asp Glu Asp Lys Pro Tyr Lys Cys Gln Leu Cys Arg Ser
            325                 330                 335

Ser Phe Arg Tyr Lys Gly Asn Leu Ala Ser His Arg Thr Val His Thr
            340                 345                 350

Gly Glu Lys Pro Tyr His Cys Ser Ile Cys Gly Ala Arg Phe Asn Arg
            355                 360                 365

Pro Ala Asn Leu Lys Thr His Ser Arg Ile His Ser Gly Glu Lys Pro
370                 375                 380

Tyr Lys Cys Glu Thr Cys Gly Ser Arg Phe Val Gln Val Ala His Leu
385                 390                 395                 400

Arg Ala His Val Leu Ile His Thr Gly Glu Lys Pro Tyr Pro Cys Pro
            405                 410                 415

Thr Cys Gly Thr Arg Phe Arg His Leu Gln Thr Leu Lys Ser His Val
            420                 425                 430

Arg Ile His Thr Gly Glu Lys Pro Tyr His Cys Asp Pro Cys Gly Leu
            435                 440                 445

His Phe Arg His Lys Ser Gln Leu Arg Leu His Leu Arg Gln Lys His
            450                 455                 460

Gly Ala Ala Thr Asn Thr Lys Val His Tyr His Ile Leu Gly Gly Pro
465                 470                 475                 480

<210> SEQ ID NO 18
<211> LENGTH: 190
<212> TYPE: DNA
<213> ORGANISM: Homo sapiens
<220> FEATURE:
<221> NAME/KEY: promoter
<222> LOCATION: (1)...(190)
<223> OTHER INFORMATION: promoter region of B-cell CLL/lymphoma 6,
      member B (BCL6B), bcl6-associated zinc finger protein, zinc finger
      protein 62 (ZNF62), ZBTB28, BAZF gene for combined bisulfite
      restriction analysis (COBRA), -95 to +95 relative to transcription
      start site

<400> SEQUENCE: 18
gaggaaggaa ggatacagac ccaggcgttc acccaccctc caccccgcc cccgacatcc    60 cggccagata aaggagccga ggccaagagg ggagagagac cccgcccccc ttaagaagag   120
aagccgcggc ccctgcagga cgggggtaag aacaagagac tgagggagcc agactcctgg   180
```

```
gtcccccaag                                                              190

<210> SEQ ID NO 19
<211> LENGTH: 121
<212> TYPE: DNA
<213> ORGANISM: Homo sapiens
<220> FEATURE:
<221> NAME/KEY: promoter
<222> LOCATION: (1)...(121)
<223> OTHER INFORMATION: promoter region of B-cell CLL/lymphoma 6,
      member B (BCL6B), bcl6-associated zinc finger protein, zinc finger
      protein 62 (ZNF62), ZBTB28, BAZF gene for bisulfite genomic
      sequencing (BGS), -72 to +49 relative to transcription start site

<400> SEQUENCE: 19
ggcgttcacc ccacctccac ccccgccccc gacatcccgg ccagataaag gagccgaggc       60
caagagggga gagagacccc gccccccttta agaagagaag ccgcggcccc tgcaggacgg    120
g                                                                      121

<210> SEQ ID NO 20
<211> LENGTH: 902
<212> TYPE: DNA
<213> ORGANISM: Homo sapiens
<220> FEATURE:
<223> OTHER INFORMATION: CpG island spanning the promoter region and the
      first exon of B-cell CLL/lymphoma 6, member B (BCL6B),
      bcl6-associated zinc finger protein, zinc finger protein 62
      (ZNF62), ZBTB28, BAZF gene, -869 to +33 relative to transcription
      start site

<400> SEQUENCE: 20
ccttgcctac ttgccgcgct ggaccccggc gtcccgccag cctccaagcg tagccgacgg       60
gcgggtgccc gaggccctcg tgagctggga ttggggggaaa gcaagcgggc tttgggcggg    120
agtccatctc tctggatccc tacaaggacc cagaagagag tcgggagcga gagaggccgg    180
acgcctaggt ctcccgagcg tctctcgccc ctccacccccc acctcggggc tttccccacc    240
tcctcgaggg gaagcagctg gcggagccgt ccggtcgcag gacaatggaa ggaaaccaac    300
tagaaatcat atccgccctc tccgtacccc gcccggccaa agccccccctt tttgtaggcc    360 cgggtagagt agcctgtcat tcacaccaca ccctcccccgt ctgagaccct acgggagccc    420
actgtcgtct gcccaaacct gctgtctcgt tgggctcccc ctttttctccc ttaacacagt    480 acaagagagg gagaggggggt tgccgtatgc actttgtcct gcagcaaagg ttggctcctg    540
gcaaaccctc ccaaaagcca acacaccaat tttcactggc ccaggccttc cgacgactca    600
gactcccgta ttgccaacct cgatatccct aacctcctcc ccaattccaa tatcccccgtc    660 ctcgtgtcca cttgcagtga cccaagaccc cctacgttac gaccaccccct tgtttctgag    720 gtcccgccct cgagacggag acccccgccct ggactcgcca tctggagagc gagggaggaa    780
ggaaggatac agacccaggc gttcacccca cctccaccccc cgcccccgac atcccggcca    840
gataaaggag ccgaggccaa gaggggagag agacccccgcc cccctttaagaa agagaagccg    900 cg                                                                     902
```